United States Patent [19]

Hagiwara et al.

[11] Patent Number: 5,589,573

[45] Date of Patent: Dec. 31, 1996

[54] AMINO ACID SEQUENCES OF ANTI-IDIOTYPIC ANTIBODIES AGAINST ANTI-CANCER HUMAN MONOCLONAL ANTIBODY, AND DNA BASE SEQUENCES ENCODING THOSE SEQUENCES

[75] Inventors: Hideaki Hagiwara, Takarazuka; Yasuyuki Aotsuka, Koube, both of Japan

[73] Assignee: Yoshihide Hagiwara, Takarazuka, Japan

[21] Appl. No.: 318,970

[22] Filed: Oct. 6, 1994

[30] Foreign Application Priority Data

Oct. 6, 1993 [JP] Japan ..................... 5-272950

[51] Int. Cl.$^6$ ............ C07K 16/42; A61K 51/10
[52] U.S. Cl. ................. 530/387.2; 530/387.1; 530/387.3; 536/25.53
[58] Field of Search ............ 530/387.1, 387.2, 530/387.3; 536/23.53

[56] References Cited

U.S. PATENT DOCUMENTS 5,208,146 5/1993 Irie .......................... 435/723
5,286,647 2/1994 Handley et al. ............ 435/240.27

FOREIGN PATENT DOCUMENTS 59-137497 8/1984 Japan.
59-135898 8/1984 Japan.
4346792 12/1992 Japan.
8900050 1/1989 WIPO.
9310221 5/1993 WIPO.

OTHER PUBLICATIONS

*Molecular Cloning*, 2nd edition ed. by Sambrook, et al., Cold Spring Harbor Laboratory Press, 1898, §7.12.
*Identification of a malignant cell* . . . , Y. Aotsuka, et al., European Journal of Cancer and Clinical Oncology, vol. 24, No. 5, pp. 829–838.
*UC 729–6* . . . , M. Glassy, et al., Proceedings of the National Academy of Sciences of the USA, vol. 80, No. 20, Oct. 1983, pp. 6327–6331.
*Quantitation of human* . . . , W. Taddei–Peters, et al., Cancer Research, vol. 52, No. 9, 1 May 1992, pp. 2603–2609.
*Immunoglobulin variable region* . . . , K. Yago, et al., Molecular Immunology, vol. 30, No. 16, Nov. 1993, pp. 1481–1489.

*Primary Examiner*—Donald E. Adams
*Attorney, Agent, or Firm*—Sherman and Shalloway

[57] ABSTRACT

Amino acid sequences of the H chain and L chain variable regions of mouse monoclonal antibodies Idio 3, Idio 17, Idio 20, Idio 27 and Idio 33 against idiotypes of a cancer cell antigen-specific human immunoglobulin CLN/IgG produced by a human/human fused cell strain CLN/SUZ H11, and base sequences of the genes of the variable regions are disclosed. The above amino acid sequences and the base sequences are useful in medical and pharmaceutical fields such as prophylaxis, treatment and/or diagnosis of human diseases, and/or in pharmacological and/or biochemical fields, etc. such as biochemical reagents, and reagents for purification of biomacromolecules.

5 Claims, 5 Drawing Sheets

FIG. 1

|  | + | λ | K | G3 | G2b | G2a | G1 | M | A |
|---|---|---|---|----|-----|-----|----|---|---|
| Idio 3 | | λ | K | G3 | G2b | G2a | G1 | M | A |
| Idio 17 | | λ | K | G3 | G2b | G2a | G1 | M | A |
| Idio 20 | | λ | K | G3 | G2b | G2a | G1 | M | A |
| Idio 27 | | λ | K | G3 | G2b | G2a | G1 | M | A |
| Idio 33 | | λ | K | G3 | G2b | G2a | G1 | M | A |

FIG. 4

|  |  | 3 | 17 | 20 | 27 | 33 |
|---|---|---|---|---|---|---|
| FR1 | 1 | Glu | Glu | Glu | Glu | Glu |
| | 2 | Val | Val | Val | Val | Val |
| | 3 | Gln | Gln | Lys | Lys | Gln |
| | 4 | Leu | Leu | Leu | Leu | Leu |
| | 5 | Gln | Gln | Val | Val | Gln |
| | 6 | Gln | Gln | Glu | Glu | Gln |
| | 7 | Ser | Ser | Ser | Ser | Ser |
| | 8 | Gly | Gly | Gly | Gly | Gly |
| | 9 | Thr | Thr | Gly | Gly | Ala |
| | 10 | Val | Val | Gly | Gly | Glu |
| | 11 | Leu | Leu | Leu | Leu | Leu |
| | 12 | Ala | Ala | Val | Val | Ala |
| | 13 | Arg | Arg | Gln | Gln | Arg |
| | 14 | Pro | Pro | Pro | Pro | Pro |
| | 15 | Gly | Gly | Gly | Gly | Gly |
| | 16 | Ala | Ala | Gly | Gly | Ala |
| | 17 | Ser | Ser | Ser | Ser | Ser |
| | 18 | Val | Val | Leu | Leu | Val |
| | 19 | Lys | Lys | Arg | Arg | Asn |
| | 20 | Met | Met | Leu | Leu | Leu |
| | 21 | Ser | Ser | Ser | Ser | Ser |
| | 22 | Cys | Cys | Cys | Cys | Cys |
| | 23 | Lys | Lys | Ala | Ala | Lys |
| | 24 | Ala | Ala | Thr | Thr | Ala |
| | 25 | Ser | Ser | Ser | Ser | Ser |
| | 26 | Gly | Gly | Gly | Gly | Gly |
| | 27 | Tyr | Tyr | Leu | Phe | Tyr |
| | 28 | Thr | Thr | Thr | Thr | Thr |
| | 29 | Phe | Phe | Phe | Phe | Phe |
| | 30 | Asn | Asn | Thr | Thr | Thr |
| CDR1 | 31 | Ser | Ser | Asp | Asp | Asn |
| | 32 | Tyr | Tyr | Tyr | Tyr | Tyr |
| | 33 | Trp | Trp | Tyr | Tyr | Trp |
| | 34 | Met | Met | Met | Met | Met |
| | 35 | His | His | Asn | Asn | Gln |
| | 36 | Trp | Trp | Trp | Trp | Trp |
| | 37 | Val | Val | Val | Val | Val |
| | 38 | Lys | Lys | Arg | Arg | Lys |
| | 39 | Gln | Gln | Gln | Gln | Gln |
| | 40 | Arg | Arg | Pro | Pro | Arg |
| | 41 | Pro | Pro | Pro | Pro | Pro |
| FR2 | 42 | Gly | Gly | Gly | Gly | Gly |
| | 43 | Gln | Gln | Lys | Lys | Gln |
| | 44 | Gly | Gly | Glu | Ala | Gly |
| | 45 | Leu | Leu | Leu | Leu | Leu |
| | 46 | Glu | Glu | Glu | Glu | Glu |
| | 47 | Trp | Trp | Trp | Trp | Trp |
| | 48 | Ile | Ile | Leu | Leu | Ile |
| CDR2 | 49 | Gly | Gly | Gly | Gly | Gly |
| | 50 | Ala | Ala | Phe | Phe | Ala |
| | 51 | Ile | Ile | Ile | Ile | Ile |
| | 52 | Tyr | Tyr | Arg | Arg | Tyr |
| | 52A | Pro | Pro | Asn | Asn | Pro |
| | 52B | --- | --- | Lys | Lys | --- |
| | 52C | --- | --- | Ala | Ala | --- |
| | 53 | Gly | Gly | Asn | Asn | Gly |
| | 54 | Asn | Asn | Leu | Tyr | Asp |
| | 55 | Ser | Ser | Tyr | Tyr | Gly |
| | 56 | Asp | Asp | Thr | Thr | Asp |
| | 57 | Ile | Ile | Thr | Thr | Thr |
| | 58 | Ser | Ser | Asp | Glu | Arg |
| | 59 | Tyr | Tyr | Tyr | Tyr | Tyr |
| | 60 | Ser | Ser | Ser | Ser | Thr |
| | 61 | Gln | Gln | Ala | Ala | Gln |
| | 62 | Asn | Asn | Ser | Ser | Lys |
| | 63 | Phe | Phe | Val | Val | Phe |
| | 64 | Lys | Lys | Lys | Lys | Lys |
| | 65 | Asp | Asp | Gly | Gly | Gly |
| | 66 | Arg | Arg | Arg | Arg | Lys |
| | 67 | Ala | Ala | Phe | Phe | Ala |
| | 68 | Lys | Lys | Thr | Thr | Thr |
| | 69 | Leu | Leu | Ile | Ile | Leu |
| | 70 | Thr | Thr | Ser | Ser | Thr |
| | 71 | Ala | Ala | Arg | Arg | Ala |
| | 72 | Val | Val | Asp | Asp | Ala |
| | 73 | Thr | Thr | Asn | Asn | Lys |
| | 74 | Ser | Ser | Pro | Ser | Ser |
| | 75 | Thr | Thr | Gln | Gln | Ser |
| | 76 | Ser | Ser | Ser | Ser | Ser |
| | 77 | Thr | Thr | Ile | Ile | Thr |
| | 78 | Ala | Ala | Leu | Leu | Ala |
| | 79 | Tyr | Tyr | Tyr | Tyr | Tyr |
| FR3 | 80 | Met | Met | Leu | Leu | Met |
| | 81 | Glu | Glu | Gln | Gln | Gln |
| | 82 | Leu | Leu | Met | Met | Leu |
| | 82A | Arg | Arg | Asn | Asn | Ser |
| | 82B | Ser | Ser | Thr | Thr | Ser |
| | 82C | Leu | Leu | Leu | Leu | Leu |
| | 83 | Thr | Thr | Thr | Arg | Ala |
| | 84 | Asn | Asn | Thr | Ala | Ser |
| | 85 | Glu | Glu | Glu | Glu | Glu |
| | 86 | Asp | Asp | Asp | Asp | Asp |
| | 87 | Ser | Ser | Ser | Ser | Ser |
| | 88 | Ala | Ala | Ala | Ala | Ala |
| | 89 | Val | Val | Thr | Thr | Val |
| | 90 | Tyr | Tyr | Tyr | Tyr | Tyr |
| | 91 | Phe | Phe | Tyr | Tyr | Tyr |
| | 92 | Cys | Cys | Cys | Cys | Cys |
| | 93 | Thr | Thr | Ala | Ala | Ala |
| | 94 | Lys | Lys | Arg | Arg | Arg |
| CDR3 | 95 | Glu | Glu | Asp | Asp | Ser |
| | 96 | Glu | Glu | Arg | Gly | Gly |
| | 97 | Tyr | Tyr | Gly | Phe | Tyr |
| | 98 | Asp | Asp | Gly | Leu | Tyr |
| | 99 | Tyr | Tyr | Arg | Arg | Gly |
| | 100 | Asp | Asp | Asp | Asp | Ser |
| | 100A | Thr | Thr | --- | --- | Phe |
| | 100B | --- | --- | --- | --- | Val |
| | 100C | --- | --- | --- | --- | Gly |
| | 100D | --- | --- | --- | --- | --- |
| | 100E | --- | --- | --- | --- | --- |
| | 100F | --- | --- | --- | --- | --- |
| | 100G | --- | --- | --- | --- | --- |
| | 100H | --- | --- | --- | --- | --- |
| | 100I | --- | --- | Trp | Trp | --- |
| | 100J | --- | --- | Tyr | Tyr | --- |
| | 100K | Leu | Leu | Phe | Phe | Phe |
| | 101 | Asp | Asp | Asp | Asp | Ala |
| | 102 | Tyr | Tyr | Val | Val | Tyr |
| FR4 | 103 | Trp | Trp | Trp | Trp | Trp |
| | 104 | Gly | Gly | Gly | Gly | Gly |
| | 105 | Gln | Gln | Ala | Ala | Gln |
| | 106 | Gly | Gly | Gly | Gly | Gly |
| | 107 | Thr | Thr | Thr | Thr | Thr |
| | 108 | Ser | Ser | Thr | Thr | Leu |
| | 109 | Val | Val | Val | Val | Val |
| | 110 | Thr | Thr | Thr | Thr | Thr |
| | 111 | Val | Val | Val | Val | Val |
| | 112 | Ser | Ser | Ser | Ser | Ser |
| | 113 | Ser | Ser | Ser | Ser | Ala |

| | | 3 | 17 | 20 | 27 | 33 |
|---|---|---|---|---|---|---|
| FR1 | 1 | Asp | Asp | Asp | Asp | Asp |
| | 2 | Ile | Ile | Ile | Ile | Ile |
| | 3 | Val | Val | Val | Val | Val |
| | 4 | Leu | Leu | Leu | Met | Met |
| | 5 | Thr | Thr | Thr | Thr | Thr |
| | 6 | Gln | Gln | Gln | Gln | Gln |
| | 7 | Ser | Ser | Ser | Ser | Ser |
| | 8 | Pro | Pro | Pro | His | His |
| | 9 | Ala | Ala | Ala | Lys | Lys |
| | 10 | Ser | Ser | Ser | Phe | Phe |
| | 11 | Leu | Leu | Leu | Met | Met |
| | 12 | Ala | Ala | Ala | Ser | Ser |
| | 13 | Val | Val | Val | Thr | Thr |
| | 14 | Ser | Ser | Ser | Ser | Ser |
| | 15 | Pro | Leu | Leu | Val | Val |
| | 16 | Leu | Gly | Gly | Gly | Gly |
| | 17 | Gly | Gln | Gln | Asp | Asp |
| | 18 | Gln | Arg | Arg | Arg | Arg |
| | 19 | Arg | Ala | Ala | Val | Val |
| | 20 | Ala | Ser | Thr | Ser | Thr |
| | 21 | Thr | Ile | Ile | Ile | Ile |
| | 22 | Ile | Ser | Ser | Thr | Thr |
| | 23 | Ser | --- | --- | Cys | Cys |
| CDR1 | 24 | Tyr | Tyr | Tyr | Lys | Lys |
| | 25 | Arg | Arg | Arg | Ala | Ala |
| | 26 | Ala | Ala | Ala | Ser | Ser |
| | 27 | Ser | Ser | Ser | Gln | Gln |
| | 27A | Lys | Lys | Lys | --- | --- |
| | 27B | Ser | Ser | Ser | --- | --- |
| | 27C | Val | Val | Val | --- | --- |
| | 27D | Gln | Ser | Ser | --- | --- |
| | 27E | Leu | Thr | Thr | --- | --- |
| | 27F | His | --- | --- | --- | --- |
| | 28 | Leu | Ser | Ser | Asp | Asp |
| | 29 | Ala | Gly | Gly | Val | Val |
| | 30 | Ile | Tyr | Tyr | Asn | Thr |
| | 31 | Val | Ser | Ser | Thr | Thr |
| | 32 | Tyr | Tyr | Tyr | Ala | Asp |
| | 33 | Met | Met | Met | Val | Val |
| | 34 | His | His | His | Ala | Ala |
| FR2 | 35 | Trp | Trp | Trp | Trp | Trp |
| | 36 | Asn | Asn | Asn | Tyr | Tyr |
| | 37 | Gln | Gln | Gln | Gln | Gln |
| | 38 | Gln | Gln | Gln | Gln | Gln |
| | 39 | Lys | Lys | Arg | Lys | Lys |
| | 40 | Pro | Pro | Pro | Pro | Pro |
| | 41 | Gly | Gly | Gly | Gly | Arg |
| | 42 | Gln | Gln | Gln | Gln | Gln |
| | 43 | Pro | Pro | Pro | Ser | Ser |
| | 44 | Pro | Pro | Pro | Pro | Pro |
| | 45 | Arg | Arg | Arg | Lys | Lys |
| | 46 | Leu | Leu | Leu | Leu | Leu |
| | 47 | Leu | Leu | Leu | Leu | Leu |
| | 48 | Ile | Ile | Ile | Leu | Ile |
| | 49 | Tyr | Tyr | Tyr | Tyr | Tyr |
| CDR2 | 50 | Leu | Leu | Leu | Ser | Ser |
| | 51 | Val | Val | Val | Ala | Ala |
| | 52 | Ser | Ser | Ser | Ser | Ser |
| | 53 | Asn | Asn | Asn | Tyr | Tyr |
| | 54 | Leu | Leu | Leu | Arg | Arg |
| | 55 | Glu | Glu | Asp | Tyr | Tyr |
| | 56 | Ser | Ser | Ser | Thr | Thr |
| | 57 | Gly | Gly | Gly | Gly | Gly |
| | 58 | Val | Val | Val | Val | Val |
| | 59 | Pro | Pro | Pro | Pro | Pro |
| | 60 | Ala | Ala | Ala | Asp | Asp |
| | 61 | Arg | Arg | Arg | His | Arg |
| | 62 | Phe | Phe | Phe | Phe | Phe |
| | 63 | Ser | Ser | Ser | Thr | Thr |
| | 64 | Gly | Gly | Gly | Gly | Gly |
| FR3 | 65 | Ser | Ser | Ser | Ser | Ser |
| | 66 | Gly | Gly | Gly | Gly | Gly |
| | 67 | Gly | Ser | Ser | Ser | Ser |
| | 68 | Gly | Gly | Gly | Gly | Gly |
| | 69 | Thr | Thr | Thr | Thr | Thr |
| | 70 | Asp | Asp | Asp | Asp | Asp |
| | 71 | Phe | Phe | Phe | Phe | Phe |
| | 72 | Thr | Thr | Thr | Thr | Thr |
| | 73 | Leu | Leu | Leu | Phe | Phe |
| | 74 | Asn | Asn | Asn | Thr | Thr |
| | 75 | Ile | Ile | Ile | Ile | Ile |
| | 76 | His | His | His | Ser | Ser |
| | 77 | Pro | Pro | Pro | Ser | Ser |
| | 78 | Val | Val | Val | Val | Val |
| | 79 | Glu | Glu | Glu | Gln | Gln |
| | 80 | Glu | Glu | Glu | Ala | Ala |
| | 81 | Glu | Glu | Glu | Glu | Glu |
| | 82 | Asp | Asp | Asp | Asp | Asp |
| | 83 | Ala | Ala | Ala | Leu | Leu |
| | 84 | Ala | Ala | Ala | Ala | Ala |
| | 85 | Thr | Thr | Thr | Val | Val |
| | 86 | Tyr | Tyr | Tyr | Tyr | Tyr |
| | 87 | Tyr | Tyr | Tyr | Tyr | Tyr |
| | 88 | Cys | Cys | Cys | Cys | Cys |
| CDR3 | 89 | Gln | Gln | Gln | Gln | Gln |
| | 90 | His | His | His | Gln | Gln |
| | 91 | Ile | Ile | Ile | His | His |
| | 92 | Arg | Arg | Glu | Tyr | Tyr |
| | 93 | Val | Gly | Gly | Ser | Ser |
| | 94 | Ala | Ala | Ala | Pro | Thr |
| | 95 | --- | --- | --- | Pro | Ala |
| | 95A | --- | --- | --- | --- | --- |
| | 95B | --- | --- | --- | --- | --- |
| | 95C | --- | --- | --- | --- | --- |
| | 95D | --- | --- | --- | --- | --- |
| | 95E | --- | --- | --- | --- | --- |
| | 95F | --- | --- | --- | --- | --- |
| | 96 | Tyr | Tyr | Tyr | Leu | Trp |
| | 97 | Thr | Thr | Thr | Thr | Thr |
| FR4 | 98 | Phe | Phe | Phe | Phe | Phe |
| | 99 | Gly | Gly | Gly | Gly | Gly |
| | 100 | Gly | Gly | Gly | Ala | Gly |
| | 101 | Gly | Gly | Gly | Gly | Gly |
| | 102 | Thr | Thr | Thr | Thr | Thr |
| | 103 | Lys | Lys | Lys | Lys | Lys |
| | 104 | Leu | Leu | Leu | Leu | Leu |
| | 105 | Glu | Glu | Glu | Glu | Glu |
| | 106 | Ile | Ile | Ile | Leu | Ile |
| | 106A | --- | --- | --- | --- | --- |
| | 107 | Lys | Lys | Lys | Lys | Lys |

FIG. 5

AMINO ACID SEQUENCES OF ANTI-IDIOTYPIC ANTIBODIES AGAINST ANTI-CANCER HUMAN MONOCLONAL ANTIBODY, AND DNA BASE SEQUENCES ENCODING THOSE SEQUENCES

DETAILED DESCRIPTION OF THE INVENTION

This invention relates to the structure of the variable regions of mouse immunoglobulins against idiotypes of an antigen-specific human immunoglobulin, useful in wide fields, for example in pharmaceutical fields such as prophylaxis, treatment and/or diagnosis of human diseases, and/or in pharmacological and/or biochemical fields such as biochemical reagents and reagents for purification of biomacromolecules.

More detailedly, this invention relates to the amino acid sequences of the H chain and L chain variable regions of mouse immunoglobulins against idiotypes of a cancer cell antigen-specific human immunoglobulin produced by a human/human fused cell strain CLN/SUZ H11 from a B cell of a patient carrying human cervical carcinoma and a human lymphoblastoid cell strain, and relates to the base sequences of the genes of the variable regions.

Since the development of the technique of formation of monoclonal antibodies by cell fusion or immortalization of cells, many useful antibodies have been obtained using mainly mice. Among them, monoclonal antibodies against malignant tumor cells are utilized not only for fundamental researches such as analyses of tumor antigens, but in serum diagnoses, image diagnoses of tumors using labeled antibodies, and have extremely high utilization value. Particularly, human-derived anti-cancer monoclonal antibodies are expected as ideal antibodies in the clinical field, since they have only faint or no side effects.

In such circumstances, one of the present inventors, as disclosed detailedly in Japanese Laid-Open Patent Publication No. 201994/1983 (=U.S. Pat. No. 5,286,647; EP-A-839,02157.3), Japanese Laid-Open Patent Publication No. 135898/1984 and Japanese Laid-Open Patent Publication No. 137497/1984, established a cell strain CLN/SUZ H11 (ATCC No. HB 8307) which produces a human monoclonal antibody having a high reactivity with human cancer cells. Interesting findings are obtained about the antibody (named CLN-IgG) produced by this cell strain, that the antibody class is IgG; the isotypes are γ1 type and κ type; and the antibody binds to a cancer antigen immunohistologically existing on the surface of the cancer cells and moreover inhibits proliferation of the cancer cells. At present, the whole amino acid sequence and DNA base sequence of the antibody are clarified (Japanese Laid-Open Patent Publication No. 346792/1992=WO 92/20799).

On the other hand, since Jerne put forward the so-called network theory, various researches have been made on the structure of the variable regions of antibodies. An antibody binds to an antigen at its variable region (antigen combining site). Therefore, the variable regions of antibodies have various three-dimensional-like structures in accordance with the structures of the antigenic determinants on the surfaces of antigens to be recognized. Thus, an antibody itself can be considered to be an antigen, and in the case, the structures of the variable regions of the antibody are called idiotypes, and antibodies against the idiotypes of the antibody are called anti-idiotypic antibodies. The structure corresponding to an antigenic determinant is called an idiotope. An idiotype can be thought to be an aggregate of idiotypes. It was reported that among anti-idiotypic antibodies (Ab2) against an antibody (Ab1) exist antibodies which competitively inhibit binding of Ab1 to an antigen and have idiotopes analogous to antigens recognized by the antibodies, i.e. antibodies having structures as so-called internal images of the antigen.

In view of the above findings, anti-idiotypic antibodies are expected to be utilized for the purpose of treatment and/or diagnosis of cancers.

For example, as for the purpose of cancer treatment, a vaccine therapy using an anti-idiotypic antibody as an antigen is made possible. It is generally difficult to get cancer antigens in large amounts, and it is restricted from a safety aspect and an ethical aspect to directly immunize human beings with cancer cells as antigens. Therefore, these problems can be avoided by performing immunization with an anti-idiotypic antibody in place of an antigen.

In a diagnostic aspect, anti-idiotypic antibodies can be utilized to examine the state of immune reactions against cancer cells. Specifically, it serves for early detection of cancers, judgment of therapeutic effects to detect or determine one's antibodies against cancer antigens existing in the blood or humor of cancer patients.

Under such technical background, problems as stated below are underlying to be solved.

1) When anti-idiotypic antibodies are utilized as vaccines or diagnostic drugs, it is necessary to provide these antibodies in large amounts and stably. 2) There is a possibility to give more powerful vaccines or diagnostic drugs abounding in functionality by altering or modifying the antibodies.

A method by gene manipulation is considered as a means for solving the above problems, i.e. a means for realizing improvement of production amount of the antibodies and elevation or modification of the activities of the antibodies.

For example, in the case of the problem of 1), it can be considered to solve the problem by cloning such an antibody gene, introducing the gene into host cells such as animal cells or *Escherichia coli*, expressing the antibody gene to give a large amount of the antibody, and in the case of the problem of 2), it can be considered to alter such an antibody so as to have stronger immunogenicity by artificially changing the antibody gene, or to design an antibody molecule having a higher vaccinal activity by adding a function which the antibody does not inherently have, for example an enzymatic activity, an immunity induction activity or the like to the antibody molecule or a fragment thereof.

For accomplishment of these purposes, separation of anti-idiotypic antibody genes, and clarification of their structures are necessary. However, there has not so far been known anything at all about the structures of L chains and H chains constituting anti-idiotypic antibodies against idiotypes of CLN-IgG, and the gene structures of the variable regions having a function to specifically bind to idiotopes of CLN-IgG.

Thus the main object of this invention is to clarify the gene structures of the L chains and the H chains of anti-CLN-IgG idiotype antibodies.

The present inventors have succeeded in creating hybridomas producing, respectively, five kinds of mouse anti-CLN-IgG idiotype antibodies (Idio 3, Idio 17, Idio 20, Idio 27 and Idio 33) having γ1 and κ isotypes against the idiotypes of CLN-IgG; have separated, from the hybridomas, cDNAs encoding the L chains and H chains of the anti-idiotypic antibodies, respectively; have clarified their DNA base sequences; have determined, based on these sequences, the amino acid sequences of the L chains and H chains of the antibodies, respectively; and have completed this invention.

Thus, according to this invention are provided an immunoglobulin H chain variable region fragment which contains a hypervariable region CDR1 having an amino acid sequence selected from (1) Ser Tyr Trp Met His; SEQ ID NO. 1 Asp Tyr Tyr Met Asn; and SEQ ID NO. 2 Asn Tyr Trp Met Gln, SEQ ID NO. 3 a hypervariable region CDR2 having an amino acid sequence selected from (2) Ala Ile Tyr Pro Gly Asn Ser Asp Ile Set Tyr Ser Gln Asn Phe Lys Asp; SEQ ID NO. 4 Phe Ile Arg Asn Lys Ala Asn Leu Tyr Thr Thr Asp Tyr Ser Ala Ser Val Lys Gly; SEQ ID NO. 5 Phe Ile Arg Asn Lys Ala Asn Tyr Tyr Thr Thr Glu Tyr Ser Ala Set Val Lys Gly; and Ala Ile Tyr Pro Gly SEQ ID NO. 6 Asp Gly Asp Thr Arg Tyr Thr Glu Lys Phe Lys Gly SEQ ID NO. 7, and a hypervariable region CDR3 having an amino acid sequence selected from (3) Glu Glu Tyr Asp Tyr Asp Thr Leu Asp Tyr; SEQ ID NO. 8 Asp Arg Gly Gly Arg Asp Trp Tyr Phe Asp Val; SEQ ID NO. 9 Asp Gly Phe Leu Arg Asp Trp Tyr Phe Asp Val; and SEQ ID NO. 10 Ser Gly Tyr Tyr Gly Ser Phe Val Gly Phe Ala Tyr; SEQ ID NO. 11 and DNA and RNA fragments encoding the immunoglobulin H chain variable region fragment.

According to this invention are further provided an immunoglobulin L chain fragment which contains a hypervariable region CDR1 having an amino acid sequence selected from (1) Tyr Arg Ala Set Lys Set Val Gln Leu His Leu Ala Ile Val Tyr Met His; SEQ ID NO. 12 Tyr Arg Ala Set Lys Ser Val Set Thr Ser Gly Tyr Ser Tyr Met His; SEQ ID NO. 13 Lys Ala Ser Gln Asp Val Asn Thr Ala Val Ala; and Lys Ala Set Gln Asp Val Thr SEQ ID NO. 14 Thr Asp Val Ala, a hypervariable region CDR2 having an amino acid sequence SEQ ID NO. 15 selected from (2) Leu Val Ser Asn Leu Glu Ser; Leu Val Set Asn Leu Asp Ser; and SEQ ID NO. 16 Ser Ala Ser Tyr Arg Tyr Thr, SEQ ID NO. 17 and a hypervariable region CDE3 having an amino acid sequence selected from (3) Gln His Ile Arg Val Ala Tyr Thr; SEQ ID NO. 19 Gln His Ile Arg Gly Ala Tyr Thr; SEQ ID NO. 20 Gln His Ile Glu Gly Ala Tyr Thr; SEQ ID NO. 21 Gln Gln His Tyr Ser Pro Pro Leu Thr; and SEQ ID NO. 22 Gln Gln His Tyr Ser Thr Ala Trp Thr; SEQ ID NO. 23 and DNA and RNA fragments encoding the immunoglobulin L chain variable region fragment.

In this invention, cytoplasmie RNAs were prepared from the five mouse hybridomas, respectively; the RNAs were converted to eDNAs by a reverse transeriptase; the antibody genes were amplified using these eDNAs as templates and using the PCR method; the amplified DNA fragments were integrated into plasmids and cloned; the base sequences of the insertion DNAs of the plasmids purified from *Escherichia coli* clones isolated were determined, and the amino acid sequences were determined based on the base sequences. These steps are further detailedly described below.

[1] Isolation of cytoplasmic RNAs

Each mouse hybridoma is cultured and proliferated in a culture medium, e.g., RDF or RPMI 1640 medium, containing 5% fetal bovine serum under a suitable condition, e.g. under a condition of 37° C. and a carbon dioxide concentration of 5%; the resultant cells are collected by centrifugation; and the cytoplasmic RNA is extracted from the cells by a conventional method, e.g. a method disclosed in 7.12 of Molecular Cloning (2nd edition, edited by Sambrook et al., Cold Spring Harbor Laboratory Press 1989). The resultant cytoplasmic RNA can further be utilized as a template for cDNA synthesis. Specifically in this invention, the cytoplasmic RNAs were extracted from mouse hybridomas No. 3, No. 17, No. 20, No. 27 and No. 33, and provided for synthesis of cDNAs.

[2] Synthesis of cDNAs

Using a cytoplasmic RNA obtained in the step of [1] as a template, a single-strand DNA complementary to the mRNA is synthesized in the presence of dATP, dGTP, dTTP and dCTP using, as a primer, an oligo dT corresponding to a poly A, or a synthetic nucleotide having a random sequence, and a reverse transcriptase. In the specific operations in the invention, cDNAs were synthesized using the cytoplasmic RNAs obtained in the step of [1] as templates and a random hexamer as a primer, respectively, and provided for the step of amplification of the antibody genes.

[3] Amplification of antibody genes by PCR

PCR reaction is performed in the presence of dATP, dGTR, dTTP, dCTP and Taq polymerase using as a template a single-strand cDNA obtained in the step of [2] and as a primer a sequence of the antibody gene (e.g., a sequence encoding a constant region, a variable region or a leader region of the antibody gene) to amplify the antibody gene. Suitably in the invention, the antibody genes were amplified using as templates the single-strand cDNAs obtained in the step of [2] and using synthetic DNA oligomers corresponding to the sequences of the leader regions and variable regions of the L chains and H chains of the antibodies, respectively.

[4] Cloning of PCR-amplified DNA fragments

A PCR-amplified DNA fragment obtained in the step of [3] is, directly or after treatment with restriction enzyme(s), ligated into one of various vectors, for example plasmid vectors such as pUC 18, pCR1000 and pCR™, phage vectors such as M 13 phage, and phagemid vectors such as pUC 118 and pBluescrpt SK⁺ to prepare a vector containing the insertion fragment. Then, *Escherichia coli* is transformed with the vector, and a colony of the *Escherichia coli* containing the targeted antibody gene fragment is obtained. The purified vector recovered from the *Escherichia coli* is provided as a sample for determination of the DNA base sequence. In the specific operations in the invention, the PCR-amplified DNA fragments obtained in the step of [3] were directly ligated, respectively, into pCR1000 and pCR™ plasmid vector; an *Escherichia coli* INVαF' was transformed with each of the resultant plasmids; and the plasmids were purified from the resultant Escherichia coli colonies, respectively.

[5] Determination of the base sequences and amino acid sequences of the DNAs

The base sequence of the DNA at the insertion site in a plasmid obtained in the step of [4] can be determined using the Maxam-Gilbert method or the Sanger method. In the invention, the pCR1000 or pCR™ plasmid vectors containing the insertion fragments were purified, respectively; their base sequences were determind by the Sanger method; and the amino acid sequences were presumed based on their base sequences, respectively.

Hereafter, this invention is further specifically described below according to examples.

Drawings referred to in Examples are briefly described as follows.

FIG. 1 is a drawing showing isotypes of monoclonal antibodies Idio 3, Idio 17, Idio 20, Idio 27 and Idio 33.

FIG. 4 is a drawing where the amino acid sequences of the H chain variable regions of monoclonal antibodies Idio 3, Idio 17, Idio 20, Idio 27 and Idio 33 are notated in parallel according to the Kabat's notation, and the regions of the hypervariable regions CDR1, CDR2 and CDR3 are determined.

FIG. 5 is a drawing where the amino acid sequences of the L chain variable regions of monoclonal antibodies Idio 3, Idio 17, Idio 20, Idio 27 and Idio 33 are notated in parallel according to the Kabat's notation, and the regions of the hypervariable regions CDR1, CDR2 and CDR3 are determined.

EXAMPLE 1

Preparation of mouse hybridomas

Figure 2:
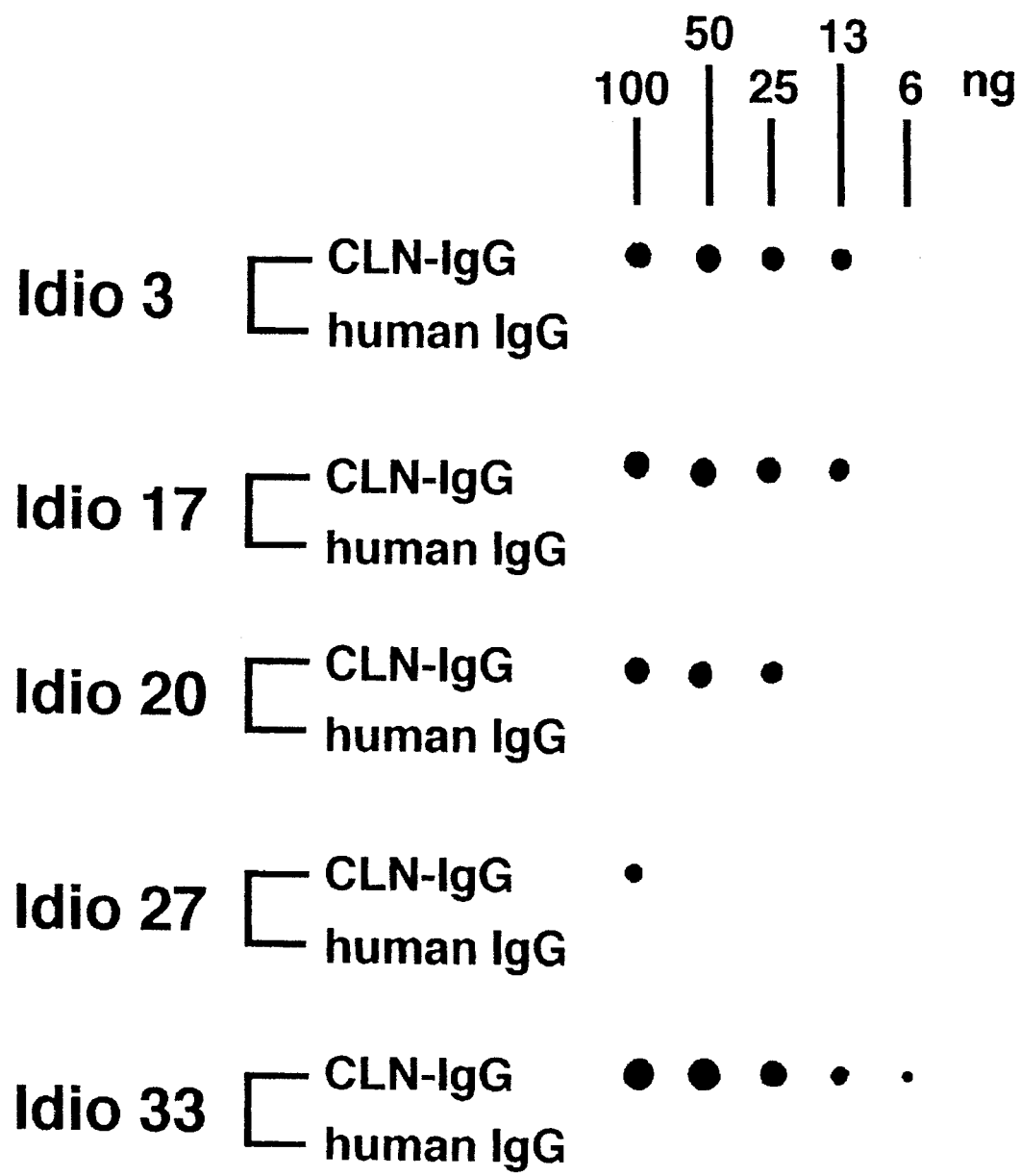
FIG. 2 is a drawing showing the monoclonal antibodies Idio 3, Idio 17, Idio 20, Idio 27 and Idio 33 specifically bind to CLN-IgG, and do not bind to other human IgGs.

100 µl of 1 mg/ml human IgG (produced by Cappel) is intraperitoneally injected to a Balb/c mouse on the first day after its birth to prepare a mouse having immunological tolerance to human IgG. Six weeks later, the mouse is immunized as follows with CLN-IgG as an antigen.

CLN-IgG purified from a culture medium of a human/human hybridoma CLN/SUZ Hl1 (ATCC No. HB8307) according to an ammonium sulfate precipitation method and protein A-affinity chromatography was adjusted to a concentration of 2 µg/µl with physiological saline; an equal amount of complete Freund's adjuvant solution was added; and after mixing and emulsification, 100 µl of the emulsion (corresponding to 100 µg of CLN-IgG) was subcutaneously injected into the immunologically tolerated mouse. Thereafter, similar immunization was repeated 4 to 5 times, the murine spleen was enucleated 4 days after the final immunization and made to be spleen cells, and they were used for the following cell fusion.

A mouse parent cells NS-1 (ATCC TIB 18) and the spleen cells are washed with portions of RPMI 1640 medium not containing serum, respectively, and the both of the cells are mixed and centrifuged. 1 ml of 50% polyethylene glycol (average molecular weight: 4,000) is added dropwise to the resultant precipitate over a period of 1 minute. 10 ml of RPMI 1640 medium is further added over a period of 3 minutes, the mixture is centrifuged at 400×g for 5 minutes, the precipitate is suspended in 10 ml of RPMI 1640 medium containing 20% fetal bovine serum, and the suspension is spread into a 96-well microplate.

Thereafter, the cells were cultured in HAT medium for 14 to 21 days, transferred to HT medium, and finally cultured in RPMI 1640 medium containins 10% fetal bovine serum.

The antibody titers in the culture supernatants on the wells where proliferation was observed were assayed by an enzyme-labeled antibody technique; hybridoma clones secreting monoclonal antibodies which bind to CLN-IgG but not to human IgG were obtained from the appropriate wells by the limiting dilution method; and these hybridoma clones were named No. 3, No. 17, No. 20, No. 27 and No. 33.

EXAMPLE 2

Determination of isotypes of the mouse antibodies

Isotypes of the antibodies secreted from the 5 mouse hybridomas obtained in Example 1 were determined as follows using a mouse monoclonal antibody isotyping kit (produced by Amersham Co.).

The mouse hybridomas are started to be cultured at a concentration each of $5 \times 10^{4}$/ml in portions of RPMI 1640 medium containing 10% fetal bovine serum, respectively, and 5 days later the culture supernatants are obtained, one stick portions of the typing sticks are placed in test tubes, respectively; 3 ml portions of the culture supernatants 5-fold diluted with TBS-T (Tris-buffered saline (TBS, pH 7.6) containing 0.1% Tween 20) are added thereto respectively; and the mixtures are incubated at room temperature for 15 minutes. The culture supernatants are discarded, 5 ml portions of TBS-T are added, and the typing sticks are washed at room temperature for 5 minutes. TBS-T was discarded, and the washing was repeated once more. 3 ml portions of a peroxidase-labeled anti-mouse antibody 500-fold diluted with TBS-T are added, and the mixtures are incubated at room temperature for 15 minutes. The typing sticks are washed twice in the same manner as above; 3 ml portions of an enzyme substrate solution (obtained by adding one drop of 30% aqueous hydrogen peroxide to 50 ml of a TBS solution of 4-chloro-1-naphtol) are added; the mixtures are subjected to reaction at room temperature for 15 minutes; and then the sticks are washed with distilled water. The isotypes of the mouse antibodies are determined based on the resultant signals, respectively.

As a result, as shown in FIG. 1, all the isotypes of these antibodies were γ1 and κ.

EXAMPLE 3

Examination of specificities of the anti-idio-typic antibodies

It was examined according to a dot blot technique, using an ECL Western blotting detecting reagent (produced by Amersham Co.), that the mouse anti-CLN-IgG idiotype antibodies specifically bind to CLN-IgG. The process is stated below.

CLN-IgG and human IgG1 (produced by Protogen Co.) were diluted with PBS to concentrations of 50 to 0.2 µl/ml, respectively. 2 µl portions of the thus prepared samples were spotted on a number of Hybond-ECL nitrocellulose membrane (produced by Amersham Co.), respectively and after being dried, the nitrocellulose membranes were allowed to stand at room temperature for one hour in PBS-T (0.3% Tween 20-containing PBS) containing 5% skim milk. After being washed with PBS-T, the nitrocellulose membranes were allowed to stand at room temperature for one hour in the culture supernatants (500-fold diluted with PBS-T) of mouse hybridomas No. 3, No. 17, No. 20, No. 27 and No. 33, respectively. After being washed with PBS-T, the nitrocellulose membranes were allowed to stand at room temperature for one hour in portions of a peroxidase-labeled sheep anti-mouse Ig antibody 3,000-fold diluted with PBS-T, respectively. After being washed with PBS-T, the nitrocellulose membranes were subjected to reaction for one minute in portions of the ECL detecting reagent, and sheets of X-ray film were exposed for 30 seconds to the light emitted from the resultant nitrocellulose membranes, respectively.

The results of the sheets of X-ray film developed are shown in FIG. 2. Any of the five antibodies bound to CLN-IgG, but did not bind to human IgG1. Namely, it was revealed that these antibodies are specific to CLN-IgG.

Next, it was examined whether or not the mouse antibodies have an activity to inhibit the binding of a human monoclonal antibody CLN-IgG to a human cancer cell. The method is stated below.

A human cervical carcinoma cell ME-180 (available from ATCC) is cultured in DF medium (a 1:1 mixed medium of DME: F-12) containing 10% fetal bovine serum. At the stage when the number of the cells becomes $5 \times 10^6$ to $1 \times 10^7$, the cells are detached from the bottom face of the Petri dish using trypsin, collected by centrifugation and sufficiently washed with the medium. A constant number ($10^5/100$ μl) each of the cells is placed in each well of a 96-well microtiter plate, and allowed to stand at 37° C. overnight to be attached on the plate. 50 μl portions of 3% glutaraldehyde solution were added dropwise into the respective wells, and the mixtures are allowed to stand at 37° C. for 20 minutes to fix the cells. The cells of each well are centrifuged at 200×g for 10 minutes and washed three times with a gelatin buffer (10 mM phosphate-buffered physiological saline containing 0.3% gelatin); 200 μl portions of 1% bovine serum albumin (BSA) solution are added dropwise; and the mixture is allowed to stand at 37° C. for one hour to block the plate. The cells are washed three times with the gelatin buffer to remove BSA not adsorbed. Thereafter, dilutions at various rates (100 to 1,000,000-fold) of the ascites obtained by intraperitoneally inoculating into mice the various hybridomas secreting the mouse anti-idiotypic antibodies are added dropwise together with CLN-IgG (50 μg each), and the mixtures are subjected to reaction at 37° C. for one hour. The cells of these wells are washed three times with the gelatin buffer, 50 μl portions of a 3,000-fold diluted peroxidase-conjugated goat anti-human Ig antibody (produced by TAGO Co.) are added dropwise, respectively, and the mixtures are subjected to reaction at 37° C. for 30 minutes. The cells are washed three times with the gelatin buffer, and portions of a substrate solution containing hydrogen peroxide and o-phenylenediamine are added to perform reaction in a darkroom. 10 minutes later, 50 μl portions of 5N sulfuric acid are added to stop the reaction. When the peroxidase-conjugated goat anti-Ig antibody remains on the microplate, namely when the human IgG to be bound thereto remains, a yellow reaction product having absorption at 490 nm is formed. The amount of CLN-IgG bound to the cancer cell is determined by measuring the amount of the reaction product by a spectrometer.

Figure 3:
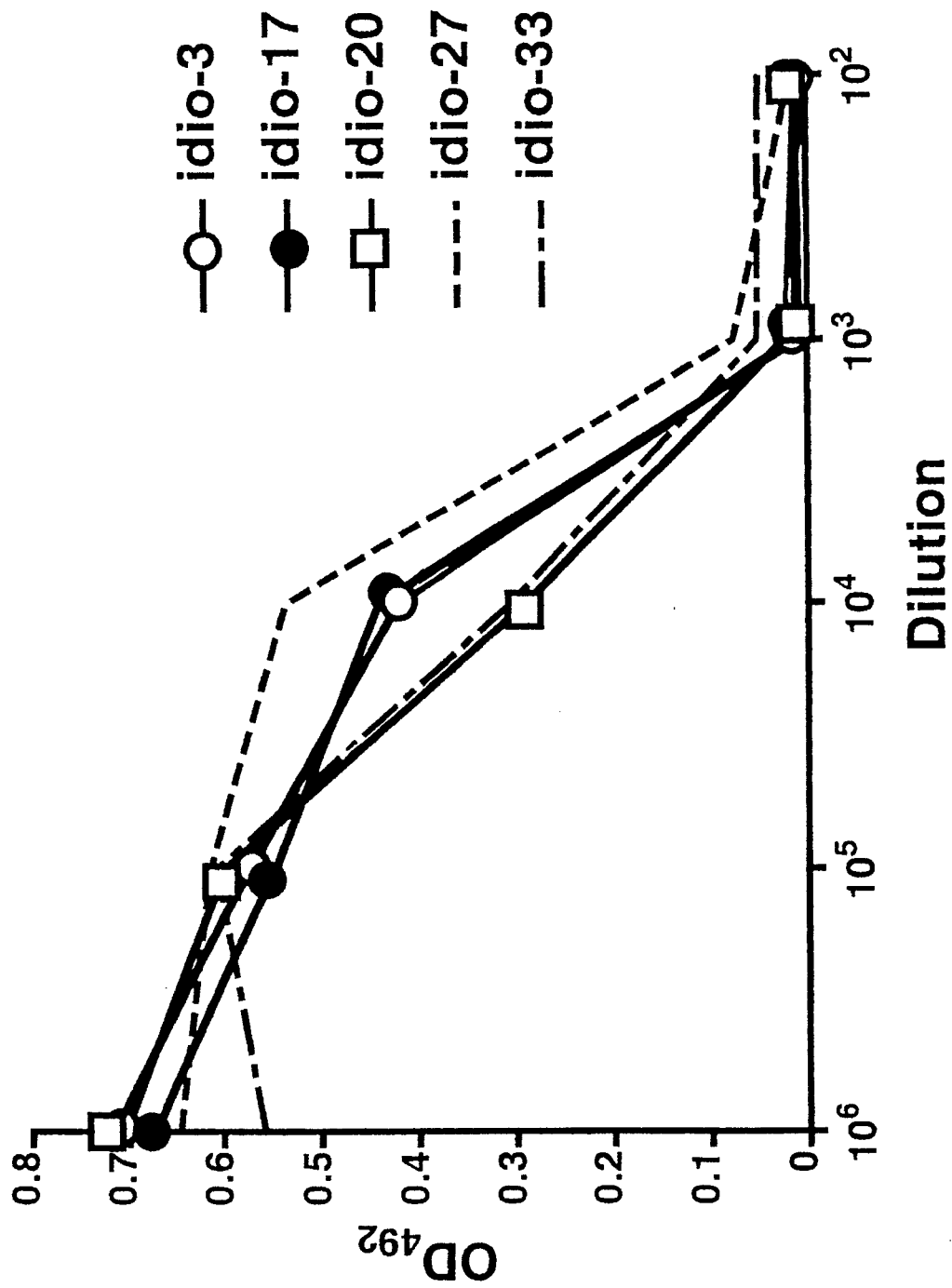
FIG. 3 is a drawing showing that monoclonal antibodies Idio 3, Idio 17, Idio 20, Idio 27 and Idio 33 are competitively inhibiting the binding between CLN-IgG and human matrical carcinoma cell ME-180.

It was clarified, according to the above method, that all the mouse antibodies Idio 3, Idio 17, Idio 20, Idio 27 and Idio 33 inhibit the binding of CLN-IgG to the cancer cell (FIG. 3).

From the foregoing, these mouse antibodies are antibodies against the idiotypes of CLN-IgG.

EXAMPLE 4

Preparation of RNA

From the five kinds of mouse hybridomas No. 3, No. 17, No. 20, No. 27 and No. 33, the cytoplasmic RNAs were extracted according to the method disclosed in Molecular Cloning (2nd edition, edited by Sambrook et al., Cold Spring Harbor Laboratory Press 1989) 7, 12, as stated below.

$10^8$ each of the hybridomas cells are collected by centrifugation, and washed twice with 10 times each precipitate's volume of a phosphate-buffered saline. The cells of these groups are centrifuged at 2,000×g and 4° C. for 5 minutes, and the resultant precipitates are suspended in 200 μl portions of an RNA extracting solution (0.14M NaCl, 1.5 mM MgCl$_2$, 10 mM Tris-HCl pH 8.6, 0.5% Nonidet P-40, 1 mM dithiothreitol, 20 mM vanadylribonucleoside complex), respectively. The suspensions are subjected to vortex for 15 seconds and allowed to stand on ice for 5 minutes. The resultant suspensions are centrifuged at 12,000×g for 30 seconds to remove the cell nuclei as precipitates; to the supernatants are, respectively, added 200 μl portions of a proteinase buffer (0.2M Tris-HCl pH 8.0, 25 mM EDTA pH 8.0, 0.3M NaCl, 1.2% SDS) and 1 μl portions of an aqueous proteinase K solution (20 mg/ml); and the mixtures are sufficiently stirred and subjected to incubation at 37° C. for 30 minutes. Equal volume portions of phenol/chloroform are added to the reaction solutions, respectively, and the mixtures are stirred, centrifuged at 5,000×g and room temperature for 10 minutes, and then allowed to separate into organic layers and aqueous layers, respectively. 400 μl portions of isopropanol cooled on ice in advance are added to the aqueous layers recovered, respectively, and the mixtures are allowed to stand on ice for 30 minutes. The mixtures are centrifuged at 12,000×g and 4° C. for 10 minutes to collect RNAs. The resultant RNA precipitates are washed with 1 ml portions of ethanol, dried under reduced pressure and suspended in appropriate amount portions of TE buffer, respectively. Using the cytoplasmic RNAs obtained according to the above operations, the antibody genes are amplified.

EXAMPLE 5

Amplification and cloning of the antibody genes by the RT-PCR method

The antibody genes were amplified from the cytoplasmic RNAs obtained in Example 4, using a GeneAmp® RNA PCR kit (produced by Takara Shuzo Co., Ltd.). First, 20 μl each of reactive solutions were prepared containing PCR buffer II (x1), 5 mM MgCl$_2$, 1 mM dATP, 1 mM dGTP, 1 mM dTTP and 1 mM dCTP, 1U/μl an RNase inhibitor, 2.5 μM a random hexamer, 2.5 U/μl a reverse transcriptase and 100 ng each of the above-mentioned cytoplasmic RNAs, respectively; 20 μl portions of a mineral oil were overlaid thereon respectively; and incubations were performed at room temperature for 10 minutes, at 42° C. for 15 minutes, at 99° C. for 5 minutes and then at 4° C. for 5 minutes to perform cDNA synthesis by reverse transcription reaction. Then, 80 μl portions of a solution consisting of 4 μl of 25 mM MgCl$_2$, 8 μl of 10×PCR buffer II, 65.5 μl of sterile distilled water, 0.5 μl of AmpliTaq DNA polymerase (5 U/μl) and 2 μl of PCR primers (each 100 pmoles) were added to the above 20 μl of the reverse transcription reaction solutions; 80 μl portions of the mineral oil were overlaid thereon; and PCR reactions were succeedingly performed. Each reaction was performed by repeating 30 times the cycle of 94° C. for 1.5 minutes, 50° C. for 2 minutes and then 72° C. for 3 minutes. The base sequences of the PCR™ primers are shown below. The primers contained in a Ig-Prime kit™ (produced by Novagen Co.) were used except for the primer of the leader sequence C for H chains.

Primer for H chains

| | | |
|---|---|---|
| Leader sequence A | 5' GGGAATTCATGRASTTSKGGYTMARCTKGRTTT 3' | SEQ ID NO. 24 |
| Leader sequence B | 5' GGGAATTCATGRAATGSASCTGGGTYWTYCTCTT 3' | SEQ ID NO. 25 |
| Leader sequence C | 5' TTAAATGGTATCCAGTGT 3' | SEQ ID NO 26 |
| Constant region | 5' CCCAAGCTTCCAGGGRCCARKGGATARACIGRTGG 3' | SEQ ID NO. 27 |

Primer for L chains

| | | |
|---|---|---|
| Leader sequence A | 5' GGGAATTCATGRAGWCACAKWCYCAGGTCTTT 3' | SEQ ID NO. 28 |
| Leader sequence B | 5' GGGAATTCATGGAGACAGACACACTCCTGCTAT 3' | SEQ ID NO. 29 |
| Constant region | 5' CCCAAGCTTACTGGATGGTGGGAAGATGGA 3' | SEQ ID NO 30 |

In the above, the letters other than A, G, C and T mean the following bases. R=A/G, W=A/T, I=inosine, Y=C/T, D=A/G/T, K=G/T, H=A/C/T, S=C/G, V=A/C/G, M=A/C, B=G/C/T 10 µl portions of the resultant 100 µl each of the PCR reaction products are subjected to 1.5% agarose gel electrophoresis, and it was confirmed that the antibody gene fragments each about 600 bp long were amplified. As a result, in the case of the H chains, the antibody genes derived from No. 3 and No. 17 were amplified in the leader sequence A, the antibody genes derived from No. 20 and No. 27 were amplified in the leader sequence B, and the antibody gene derived from No. 33 was amplified in the leader sequence C. On the other hand, in the L chains, the antibody genes derived from No. 27 and No. 33 were amplified in the case where the leader sequence A was used, and the antibody genes derived from No. 3, No. 17 and No. 20 were amplified in the leader sequence B.

Each of the PCR-amplified fragments about 600 bp long was integrated into pCR 1000 vector or pCR™ vector using TA cloning kit (produced by Invitogen Co.). Specifically, ligation mix solutions were prepared by mixing 1 µl portions of the PCR reaction products, 1 µl portions of 10×the ligation buffer, 2 µl portions of pCR1000 or pCR™ vector (corresponding to 50 µg), 1 µl of T4 DNA ligase and 6 µl portions of sterilized water, respectively; and incubated overnight at 12° C.. Separately, 50 µl portions of a suspension of a competent Escherichia coli INαT strain, to which portions were added 2 µl portions of 0.5M β-mercaptoethanol, respectively, were prepared; and 1 µl portions of the above ligation mix solutions are added thereto, respectively. The mixtures are allowed to stand on ice for 30 minutes, incubated at 42° C. for one minute, and rapidly cooled on ice for 2 minutes. 450 µl portions of SOC medium warmed to 42° C. in advance were added to the resultant Escherichia coli solutions, respectively, and the mixtures are cultured with shaking at 37° C. for one hour. Meanwhile, 25 µl portions of X-Gal (40 mg/µl) are spreaded onto a number of LB agar plates each containing Kanamycin (50 µg/ml), respectively, and the agar plates are incubated at 37° C. until each X-Gal completely permeates the agar plate.

200 µl portions of the Escherichia coli culture broths after completion of culture were spread on the agar plate dried, respectively, and the plates were allowed to stand at 37° C. overnight to give white colonies each having Kanamycin resistance.

Plasmids were purified from the Escherichia coli clones containing the respective antibody genes, and named 3KB11, 17KB1, 20KB1, 27KA2, 33KA26, 3GB1, 17GB7, 20GA2, 27GA5 and 33GC003, respectively. Purification of the plasmids is performed as follows.

The Escherichia coli strains containing the above plasmids, respectively, are cultured 37° C. overnight in 100 ml portions of LB medium containing Kanamycin (50 µg/ml), respectively. Each of the resultant culture broths is centrifuged at 3,000 rpm for 10 minutes; the cells collected are suspended in 3 ml of an ice-cooled suspension (50 mM glucose, 10 mM EDTA, 2 mM Tris-HCl pH 8.0); and the suspension is allowed to stand at room temperature for 5 minutes. 6 ml of an alkali lysing solution (0.2 N sodium hydroxide, 1% SDS) is added, and the mixture is mixed by gently turning the centrifugation vessel upside down, and allowed to stand on ice for 5 minutes. 4.5 ml of an ice-cooled neutralizing solution (5M potassium acetate pH 4.8) is added, and the mixture is centrifuged at 12,000 rpm and 4° C. for 10 minutes. The supernatant is transferred into another centrifugation vessel; 1 ml of heat-treated 100 µg/ml RNase A solution is added; and the mixture is subjected to reaction for one hour in an incubator of 37° C. to perform RNA digestion. To the reaction solution are added 6 ml of TE buffer-saturated phenol and 6 ml of chloroform/isoamyl alcohol (24:1), and the mixture is subjected to vortex for 30 seconds and then centrifuged at 10,000 rpm and 4° C. for 3 minutes. The aqueous layer is transferred into another centrifugation vessel, an equal amount of isopropanol is added, and the mixture is sufficiently mixed and then centrifuged at 10,000 rpm and room temperature for 10 minutes.

The resultant precipitate is washed with 1 ml of 70% cold (−20° C.) ethanol, dried under reduced pressure, and dissolved in 480 µl of sterilized water. The solution is transferred into an Eppendorf tube; 120 µl of 4M NaCl and 600 µl of 13% polyethylene glycol #6000 are added; and the mixture is allowed to stand on ice for 20 minutes. The mixture is then centrifuged at 10,000 rpm and 4° C. for 10 minutes, and the precipitate is washed with 1 ml of 70% cold (−20° C.) ethanol, dried under reduced pressure and dissolved in 100 µl of TE buffer. The resultant purified plasmid was used as a template for sequencing reaction.

EXAMPLE 6

Determination of the base sequences

Sanger reactions were performed using as templates the plasmids cloning purified in Example 5 and a fluorescent-labeled primer; the reaction products were analyzed by a DNA sequencer DSQ-1 (produced by Shimadzu Corporation); and the DNA base sequences of the insert parts of the plasmids were also determined.

The sequencing reactions were performed using Ampli-Taq cycle sequencing kit (produced by Takara Shuzo Co., Ltd.) and a fluorescent-labeled primer in a reagent kit (produced by Wakunaga Pharmaceutical Co., Ltd.) exclusively used for a fluorencene-type DNA sequencer. First, 2 to 4 µg of one of the plasmids purified as stated in Example 5 is mixed with 1 µl of the FITC-labeled primer (1 p mole/µl, forward or reverse is used) and 2 µl of the 10×cycling mix solution, and sterilized water is added to prepare 10 µl in final volume of a reaction mix. Four tubes are prepared in which 2 μl portions of the termination mix (A, G, C, T) were placed in advance, respectively. 2 μl portions of the above reaction mix were taken and placed into the respective tubes. The mixtures are corrected by centrifugation, 10 μl portions of a mineral oil are overlaid, and cycling reactions are performed under the following conditions; Precycle 95° C., 3 minutes; first cycle 95° C. 30 seconds, 60° C. 30 seconds, 72° C. 1 minute (repeated 15 times); second cycle 95° C. 30 seconds, 72° C. 1 minute (repeated 15 times); postcycle 4° C.

2 μl portions of a reaction-stopping dye solution (95% formaldehyde, 20 mM EDTA, 0.05% methyl violet) are added, and the mixtures are mixed by centrifugation and preserved at 20° C. until they are electrophoresed.

A 5% polyacrylamide gel was used and was obtained by adding pure water to 30 g of urea, 6 ml of 10×TBE buffer (0.89M Tris-HCl, 0.89M boric acid, 0.025M EDTA disodium salt) and 10 ml of 30% acrylamide solution (28.5% acrylamide and 1.5% methylenebisacrylamide, both produced by BIO-RAD Co.) to make the whole volume 60 ml; filtering the mixture with 0.22-μm filter; deaerating the filtrate for 30 minutes; adding 150 μl of 10% ammonium persulfate and 15 μl of TEMEO; allowing the mixture to stand overnight to make it gel.

The gel was set in the DNA sequencer DSQ-1, and prerun was performed at a constant voltage of 1,000 V for one hour. Each of the samples was denatured at 95° C. for 3 minutes immediately before electrophoresis, and rapidly cooled on ice, and 2 to 3 μl of the reaction solution was sucked up from the bottom part of the tube by a microsyringe and loaded onto the gel. Electrophoresis was performed at a constant electric power of 20 W for 12 hours.

After completion of electrophoresis, the base sequence was determined using the software attached to DSO-1. The sequence was confirmed by sequencing both of the sense and antisense chains of the same plasmid in both directions.

The resultant base sequences of the variable regions of the H chains and L chains of the five kinds of the mouse monoclonal antibodies, and amino acid sequences presumed therefrom are shown in the following sequence listing. Relation between the sequence numbers and the sequences of the clones are as follows:

Sequence No. 31 and SEQ ID NO. 40: Idio 3 H chain variable region (clone 3GB1)

Sequence No. 31 and SEQ ID NO. 41: Idio 17 H chain variable region (clone 17GB7)

Sequence No. 32 and SEQ ID NO. 42: Idio 20 H chain variable region (clone 20GA2)

Sequence No. 33 and SEQ ID NO. 43: Idio 27 H chain variable region (clone 27GA5)

Sequence No. 34: Idio 33 H chain variable region (clone 33GC003)

Sequence No. 35 and SEQ ID NO. 44: Idio 3 L chain variable region (clone 3KB11)

Sequence No. 36 and SEQ ID NO. 45: Idio 17 L chain variable region (clone 17KB1)

Sequence No. 37 and SEQ ID NO. 46: Idio 20 L chain variable region (clone 20KB1)

Sequence No. 38 and SEQ ID NO. 48: Idio 27 L chain variable region (clone 27KA2)

Sequence No. 39 and SEQ ID NO. 48: Idio 33 L chain variable region (clone 33KA26)

EXAMPLE 7

Determination of hypervariable regions

The amino acid sequences obtained in Example 6 were notated in parallel according to the numbering of Kabat et al.'s data base (Sequences of proteins of immunological interest Fifth edition, U. S. Department of health and human services. Public health service, National Institutes of Health. NIH Publication No. 91-3242, Kabat et al. 1991), and the amino acid sequences of the hypervariable regions CDR1, CDR2 and CDR3 of each antibody were identified (FIG. 4, H chains, FIG. 5 L chains). In order to confirm the novelty of the identified amino acid sequences of the hypervariable regions CDR1, CDR2 and CDR3, retrieval by a computer was performed using the above Kabat et al.'s data base and a protein data base NBRF-PDB (National Biomedical Research Foundation—protein data base) Release 36.

As a result, the amino acid sequences of Idio 3 H chain CDR1, Idio 17 H chain CDR1, Idio 20 H chain CDR1, Idio 27 H chain CDR1, Idio 33 H chain CDR2, Idio 3 L chain CDR2, Idio 17 L chain CDR2, Idio 27 L chain CDR2 and Idio 33 L chain CDR2 were the same as those of known antibodies, but the amino acid sequences of other CDRs were revealed to be novel sequences.

What is claimed is:

1. An Fv region fragment comprising the immunoglobulin H chain variable region fragment having the formula of SEQ ID No. 31 and the immunoglobulin L chain variable region fragment having the formula of SEQ ID No. 35.

2. An Fv region fragment comprising the immunoglobulin H chain variable region fragment having the formula of SEQ ID No. 31 and the immunoglobulin L chain variable region fragment having the formula of SEQ ID No. 36.

3. An Fv region fragment comprising the immunoglobulin H chain variable region fragment having the formula of SEQ ID No. 33 and the immunoglobulin L chain variable region fragment having the formula of SEQ ID No. 37.

4. An Fv region fragment comprising the immunoglobulin H chain variable region fragment having the formula of SEQ ID No. 32 and the immunoglobulin L chain variable region fragment having the formula of SEQ ID No. 38.

5. An Fv region fragment comprising the immunoglobulin H chain variable region fragment having the formula of SEQ ID No. 34 and the immunoglobulin L chain variable region fragment having the formula of SEQ ID No. 39.

* * * * *

SEQUENCE LISTING ( 1 ) GENERAL INFORMATION:

( i i i ) NUMBER OF SEQUENCES:48

( 2 ) INFORMATION FOR SEQ ID NO: 1:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR1-1
        ( D ) OTHER INFORMATION:hypervariable region ( x i ) SEQUENCE DESCRIPTION:SEQ ID NO:1:

Ser Tyr Trp Met His
            5

( 2 ) INFORMATION FOR SEQ ID NO: 2:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR1-2
        ( D ) OTHER INFORMATION:hypervariable region ( x i ) SEQUENCE DESCRIPTION:SEQ ID NO: 2:

Asp Tyr Tyr Met Asn
            5

( 2 ) INFORMATION FOR SEQ ID NO: 3:

( i ) SEQUENCE CHARACTERISTICS:
        ( A ) LENGTH:5 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR1-3
        ( D ) OTHER INFORMATION:hypervariable region ( x i ) SEQUENCE DESCRIPTION:SEQ ID NO:3:

Asn Tyr Trp Met Gln
            5

( 2 ) INFORMATION FOR SEQ ID NO: 4:

( i ) SEQUENCE CHARACTERISTICS:
        ( A ) LENGTH:17 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR2-1
        ( D ) OTHER INFORMATION:hypervariable region ( x i ) SEQUENCE DESCRIPTION:SEQ ID NO: 4:

Ala Ile Tyr Pro Gly Asn Ser Asp Ile Ser Tyr Ser Gln Asn Phe Lys
            5                   10                  15
Asp ( 2 ) INFORMATION FOR SEQ ID NO: 5:

( i ) SEQUENCE CHARACTERISTICS:
        ( A ) LENGTH:19 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR2-2
        ( D ) OTHER INFORMATION:hypervariable region ( x i ) SEQUENCE DESCRIPTION:SEQ ID NO:5:

Phe Ile Arg Asn Lys Ala Asn Leu Tyr Thr Thr Asp Tyr Ser Ala Ser ( 2 ) INFORMATION FOR SEQ ID NO: 6:

( i ) SEQUENCE CHARACTERISTICS:
        ( A ) LENGTH:19 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR2-3
        ( D ) OTHER INFORMATION:hypervariable region ( x i ) SEQUENCE DESCRIPTION:SEQ ID NO: 6:

Phe Ile Arg Asn Lys Ala Asn Tyr Tyr Thr Thr Glu Tyr Ser Ala Ser
Val Lys Gly ( 2 ) INFORMATION FOR SEQ ID NO: 7:

( i ) SEQUENCE CHARACTERISTICS:
        ( A ) LENGTH:17 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR2-4
        ( D ) OTHER INFORMATION:hypervariable region ( x i ) SEQUENCE DESCRIPTION:SEQ ID NO:7:

Ala Ile Tyr Pro Gly Asp Gly Asp Thr Arg Tyr Thr Glu Lys Phe Lys
Gly ( 2 ) INFORMATION FOR SEQ ID NO: 8:

( i ) SEQUENCE CHARACTERISTICS:
        ( A ) LENGTH:10 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR3-1
        ( D ) OTHER INFORMATION:hypervariable region ( x i ) SEQUENCE DESCRIPTION:SEQ ID NO: 8:

Glu Glu Tyr Asp Tyr Asp Thr Leu Asp Tyr ( 2 ) INFORMATION FOR SEQ ID NO: 9:

( i ) SEQUENCE CHARACTERISTICS:
        ( A ) LENGTH:11 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR3-2
        ( D ) OTHER INFORMATION:hypervariable region ( x i ) SEQUENCE DESCRIPTION:SEQ ID NO:9:

Asp Arg Gly Gly Arg Asp Trp Tyr Phe Asp Val
                  5                   10

( 2 ) INFORMATION FOR SEQ ID NO: 10:

( i ) SEQUENCE CHARACTERISTICS:
        ( A ) LENGTH:11 amino acids
        ( B ) TYPE:amino acid
        ( D ) TOPOLOGY:linear ( i i ) MOLECULE TYPE:protein ( i x ) FEATURE:
        ( A ) NAME/KEY:H-CDR3-3
        ( D ) OTHER INFORMATION:hypervariable region ( x i ) SEQUENCE DESCRIPTION:SEQ ID NO: 10:

Asp Gly Phe Leu Arg Asp Trp Tyr Phe Asp Val
                  5                   10

( 2 ) INFORMATION FOR SEQ ID NO: 11:

( i ) SEQUENCE CHARACTERISTICS:
        ( A ) LENGTH:12 amino acids
        ( B ) TYPE:amino acid
        ( D ) TOPOLOGY:linear ( i i ) MOLECULE TYPE:protein ( i x ) FEATURE:
        ( A ) NAME/KEY:H CDR3-4
        ( D ) OTHER INFORMATION:hypervariable region ( x i ) SEQUENCE DESCRIPTION:SEQ ID NO:11:

Ser Gly Tyr Tyr Gly Ser Phe Val Gly Phe Ala Tyr
                  5                   10

( 2 ) INFORMATION FOR SEQ ID NO: 12:

( i ) SEQUENCE CHARACTERISTICS:
        ( A ) LENGTH:17 amino acids
        ( B ) TYPE:amino acid
        ( D ) TOPOLOGY:linear ( i i ) MOLECULE TYPE:protein ( i x ) FEATURE:
        ( A ) NAME/KEY:L CDR1-1
        ( D ) OTHER INFORMATION:hypervariable region ( x i ) SEQUENCE DESCRIPTION:SEQ ID NO: 12:

Tyr Arg Ala Ser Lys Ser Val Gln Leu His Leu Ala Ile Val Tyr Met
                  5                   10                  15

His ( 2 ) INFORMATION FOR SEQ ID NO: 13:

( i ) SEQUENCE CHARACTERISTICS:
        ( A ) LENGTH:16 amino acids
        ( B ) TYPE:amino acid
        ( D ) TOPOLOGY:linear ( i i ) MOLECULE TYPE:protein ( i x ) FEATURE:
        ( A ) NAME/KEY:L CDR1-2
        ( D ) OTHER INFORMATION:hypervariable region ( x i ) SEQUENCE DESCRIPTION:SEQ ID NO:13:

Tyr Arg Ala Ser Lys Ser Val Ser Thr Ser Gly Tyr Ser Tyr Met His ( 2 ) INFORMATION FOR SEQ ID NO: 14:

( i ) SEQUENCE CHARACTERISTICS:
        ( A ) LENGTH:11 amino acids
        ( B ) TYPE:amino acid
        ( D ) TOPOLOGY:linear ( i i ) MOLECULE TYPE:protein ( i x ) FEATURE:
        ( A ) NAME/KEY:L CDR1-3
        ( D ) OTHER INFORMATION:hypervariable region ( x i ) SEQUENCE DESCRIPTION:SEQ ID NO: 14:

Lys Ala Ser Gln Asp Val Asn Thr Ala Val Ala
                5                    10

( 2 ) INFORMATION FOR SEQ ID NO: 15:

( i ) SEQUENCE CHARACTERISTICS:
        ( A ) LENGTH:11 amino acids
        ( B ) TYPE:amino acid
        ( D ) TOPOLOGY:linear ( i i ) MOLECULE TYPE:protein ( i x ) FEATURE:
        ( A ) NAME/KEY:L CDR1-4
        ( D ) OTHER INFORMATION:hypervariable region ( x i ) SEQUENCE DESCRIPTION:SEQ ID NO:15:

Lys Ala Ser Gln Asp Val Thr Thr Asp Val Ala
                5                    10

( 2 ) INFORMATION FOR SEQ ID NO: 16:

( i ) SEQUENCE CHARACTERISTICS:
        ( A ) LENGTH:7 amino acids
        ( B ) TYPE:amino acid
        ( D ) TOPOLOGY:linear ( i i ) MOLECULE TYPE:protein ( i x ) FEATURE:
        ( A ) NAME/KEY:L CDR2-1
        ( D ) OTHER INFORMATION:hypervariable region ( x i ) SEQUENCE DESCRIPTION:SEQ ID NO: 16:

Leu Val Ser Asn Leu Glu Ser
                5

( 2 ) INFORMATION FOR SEQ ID NO: 17:

( i ) SEQUENCE CHARACTERISTICS:
        ( A ) LENGTH:7 amino acids
        ( B ) TYPE:amino acid
        ( D ) TOPOLOGY:linear ( i i ) MOLECULE TYPE:protein ( i x ) FEATURE:
        ( A ) NAME/KEY:L CDR2-2
        ( D ) OTHER INFORMATION:hypervariable region ( x i ) SEQUENCE DESCRIPTION:SEQ ID NO:17:

Leu Val Ser Asn Leu Asp Ser
                5

( 2 ) INFORMATION FOR SEQ ID NO: 18:

( i ) SEQUENCE CHARACTERISTICS:
                   ( A ) LENGTH:7 amino acids
                   ( B ) TYPE:amino acid
                   ( D ) TOPOLOGY:linear ( i i ) MOLECULE TYPE:protein ( i x ) FEATURE:
                   ( A ) NAME/KEY:L CDR2-3
                   ( D ) OTHER INFORMATION:hypervariable region ( x i ) SEQUENCE DESCRIPTION:SEQ ID NO: 18:

Ser  Ala  Ser  Tyr  Arg  Tyr  Thr
                     5

( 2 ) INFORMATION FOR SEQ ID NO: 19:

( i ) SEQUENCE CHARACTERISTICS:
                   ( A ) LENGTH:8 amino acids
                   ( B ) TYPE:amino acid
                   ( D ) TOPOLOGY:linear ( i i ) MOLECULE TYPE:protein ( i x ) FEATURE:
                   ( A ) NAME/KEY:L CDR3-1
                   ( D ) OTHER INFORMATION:hypervariable region ( x i ) SEQUENCE DESCRIPTION:SEQ ID NO:19:

Gln  His  Ile  Arg  Val  Ala  Tyr  Thr
                     5

( 2 ) INFORMATION FOR SEQ ID NO: 20:

( i ) SEQUENCE CHARACTERISTICS:
                   ( A ) LENGTH:8 amino acids
                   ( B ) TYPE:amino acid
                   ( D ) TOPOLOGY:linear ( i i ) MOLECULE TYPE:protein ( i x ) FEATURE:
                   ( A ) NAME/KEY:L CDR3-2
                   ( D ) OTHER INFORMATION:hypervariable region ( x i ) SEQUENCE DESCRIPTION:SEQ ID NO: 20:

Gln  His  Ile  Arg  Gly  Ala  Tyr  Thr
                     5

( 2 ) INFORMATION FOR SEQ ID NO: 21:

( i ) SEQUENCE CHARACTERISTICS:
                   ( A ) LENGTH:8 amino acids
                   ( B ) TYPE:amino acid
                   ( D ) TOPOLOGY:linear ( i i ) MOLECULE TYPE:protein ( i x ) FEATURE:
                   ( A ) NAME/KEY:L CDR3-3
                   ( D ) OTHER INFORMATION:hypervariable region ( x i ) SEQUENCE DESCRIPTION:SEQ ID NO:21:

Gln  His  Ile  Glu  Gly  Ala  Tyr  Thr
                     5

( 2 ) INFORMATION FOR SEQ ID NO: 22:

( i ) SEQUENCE CHARACTERISTICS:
                   ( A ) LENGTH:9 amino acids
                   ( B ) TYPE:amino acid ( D ) TOPOLOGY:linear ( i i ) MOLECULE TYPE:protein ( i x ) FEATURE:
    ( A ) NAME/KEY:L CDR3-4
    ( D ) OTHER INFORMATION:hypervariable region ( x i ) SEQUENCE DESCRIPTION:SEQ ID NO: 22:

Gln  Gln  His  Tyr  Ser  Pro  Pro  Leu  Thr
                       5

( 2 ) INFORMATION FOR SEQ ID NO: 23:

( i ) SEQUENCE CHARACTERISTICS:
        ( A ) LENGTH:9 amino acids
        ( B ) TYPE:amino acid
        ( D ) TOPOLOGY:linear ( i i ) MOLECULE TYPE:protein ( i x ) FEATURE:
        ( A ) NAME/KEY:L CDR3-5
        ( D ) OTHER INFORMATION:hypervariable region ( x i ) SEQUENCE DESCRIPTION:SEQ ID NO:23:

Gln  Gln  His  Tyr  Ser  Thr  Ala  Trp  Thr
                       5

( 2 ) INFORMATION FOR SEQ ID NO: 24:

( i ) SEQUENCE CHARACTERISTICS:
        ( A ) LENGTH:33 base pairs
        ( B ) TYPE:nucleic acid
        ( C ) STRANDEDNESS:single
        ( D ) TOPOLOGY:linear ( i i ) MOLECULE TYPE:cDNA ( i i i ) HYPOTHETICAL:no ( i x ) FEATURE:
        ( A ) NAME/KEY:H Leader Seq. A
        ( B ) OTHER INFORMATION:R is A or G;
            S is C or G;
            K is G or T;
            Y is C or T;
            M is A or C.

( x i ) SEQUENCE DESCRIPTION:SEQ ID NO: 24:

GGGAATTCAT  GRASTTSKGG  YTMARCTKGR  TTT                        33

( 2 ) INFORMATION FOR SEQ ID NO: 25:

( i ) SEQUENCE CHARACTERISTICS:
        ( A ) LENGTH:34 base pairs
        ( B ) TYPE:nucleic acid
        ( C ) STRANDEDNESS:single
        ( D ) TOPOLOGY:linear ( i i ) MOLECULE TYPE:cDNA ( i i i ) HYPOTHETICAL:no ( i v ) ANTI-SENSE:no ( i x ) FEATURE:
        ( A ) NAME/KEY:H Leader Sequence B
        ( B ) OTHER INFORMATION:S is C or G;
            Y is C or T;
            W is A or T; and
            R is A or G.

( x i ) SEQUENCE DESCRIPTION:SEQ ID NO:25:

GGGAATTCAT GRAATGSASC TGGGTYWTYC TCTT                                       34

(2) INFORMATION FOR SEQ ID NO: 26:

(i) SEQUENCE CHARACTERISTICS:
        (A) LENGTH:18 base pairs
        (B) TYPE:nucleic acid
        (C) STRANDEDNESS:single
        (D) TOPOLOGY:linear (ii) MOLECULE TYPE:cDNA (iii) HYPOTHETICAL:no (iv) ANTI-SENSE:no (ix) FEATURE:
        (A) NAME/KEY:H Leader Sequence C (xi) SEQUENCE DESCRIPTION:SEQ ID NO: 26:

TTAAATGGTA TCCAGTGT                                                         18

(2) INFORMATION FOR SEQ ID NO: 27:

(i) SEQUENCE CHARACTERISTICS:
        (A) LENGTH:35 base pairs
        (B) TYPE:nucleic acid
        (C) STRANDEDNESS:single
        (D) TOPOLOGY:linear (ii) MOLECULE TYPE:cDNA (iii) HYPOTHETICAL:no (iv) ANTI-SENSE:no (ix) FEATURE:
        (A) NAME/KEY:H Constant Region
        (B) OTHER INFORMATION:R is A or G;
            K is G or T; and
            N is inosine.

(xi) SEQUENCE DESCRIPTION:SEQ ID NO:27:

CCCAAGCTTC CAGGGRCCAR KGGATARACN GRTGG                                      35

(2) INFORMATION FOR SEQ ID NO: 28:

(i) SEQUENCE CHARACTERISTICS:
        (A) LENGTH:32 base pairs
        (B) TYPE:nucleic acid
        (C) STRANDEDNESS:single
        (D) TOPOLOGY:linear (ii) MOLECULE TYPE:cDNA (iii) HYPOTHETICAL:no (iv) ANTI-SENSE:no (ix) FEATURE:
        (A) NAME/KEY:L Leader Sequence A
        (B) OTHER INFORMATION:R is A or G;
            K is G or T;
            W is A or T; and
            Y is C or T.

(xi) SEQUENCE DESCRIPTION:SEQ ID NO: 28:

GGGAATTCAT GRAGWCACAK WCYCAGGTCT TT                                         32

(2) INFORMATION FOR SEQ ID NO: 29:

(i) SEQUENCE CHARACTERISTICS:

(A) LENGTH:33 base pairs
(B) TYPE:nucleic acid
(C) STRANDEDNESS:single
(D) TOPOLOGY:linear (ii) MOLECULE TYPE:cDNA (iii) HYPOTHETICAL:no (iv) ANTI-SENSE:no (ix) FEATURE:
(A) NAME/KEY:L Leader Sequence B (xi) SEQUENCE DESCRIPTION:SEQ ID NO: 29:

GGAATTCAAT GGAGACAGAC ACACTCCTGC TAT  33

(2) INFORMATION FOR SEQ ID NO: 30:

(i) SEQUENCE CHARACTERISTICS:
(A) LENGTH:30 base pairs
(B) TYPE:nucleic acid
(C) STRANDEDNESS:single
(D) TOPOLOGY:linear (ii) MOLECULE TYPE:cDNA (iii) HYPOTHETICAL:no (iv) ANTI-SENSE:no (ix) FEATURE:
(A) NAME/KEY:L constant (xi) SEQUENCE DESCRIPTION:SEQ ID NO: 30:

CCCAAGCTTA CTGGATGGTG GGAAGATGGA  30

(2) INFORMATION FOR SEQ ID NO: 31:

(i) SEQUENCE CHARACTERISTICS:
(A) LENGTH:357 base pairs
(B) TYPE:nucleic acid
(C) STRANDEDNESS:double
(D) TOPOLOGY:linear (ii) MOLECULE TYPE:mRNA (iii) HYPOTHETICAL:no (iv) ANTI-SENSE:no (vi) ORIGINAL SOURCE:
(A) ORGANISM:mouse (ix) FEATURE:
(A) NAME/KEY:Idio 3 H chain variable/Idio 17 H chain variable (xi) SEQUENCE DESCRIPTION:SEQ ID NO: 31:

| GAG | GTT | CAG | CTC | GAG | CAG | TCT | GGG | ACT | GTG | CTG | GCA | AGG | CCT | GGG | GCT | 48 |
| Glu | Val | Gln | Leu | Gln | Gln | Ser | Gly | Thr | Val | Leu | Ala | Arg | Pro | Gly | Ala | |
| | | | | 5 | | | | | 10 | | | | | 15 | | |

| TCA | GTG | AAG | ATG | TCC | TGC | AAG | GCT | TCG | GGC | TAC | ACC | TTT | AAC | AGC | TAC | 96 |
| Ser | Val | Lys | Met | Ser | Cys | Lys | Ala | Ser | Gly | Tyr | Thr | Phe | Asn | Ser | Tyr | |
| | | | 20 | | | | | 25 | | | | | 30 | | | |

| TGG | ATG | CAC | TGG | GTA | AAA | CAG | AGG | CCT | GGA | CAG | GGT | CTG | GAA | TGG | ATT | 144 |
| Trp | Met | His | Trp | Val | Lys | Gln | Arg | Pro | Gly | Gln | Gly | Leu | Glu | Trp | Ile | |
| | | 35 | | | | | 40 | | | | | 45 | | | | |

| GGC | GCG | ATT | TAT | CCT | GGA | AAT | AGT | GAT | ATT | AGC | TAC | AGC | CAG | AAC | TTT | 192 |
| Gly | Ala | Ile | Tyr | Pro | Gly | Asn | Ser | Asp | Ile | Ser | Tyr | Ser | Gln | Asn | Phe | |
| | 50 | | | | | 55 | | | | | 60 | | | | | |

```
AAG  GAC  AGG  GCC  AAA  CTG  ACT  GCC  GTC  ACA  TCC  ACC  AGC  ACT  GCC  TAC       240
Lys  Asp  Arg  Ala  Lys  Leu  Thr  Ala  Val  Thr  Ser  Thr  Ser  Thr  Ala  Tyr
65             70                  75                            80

ATG  GAA  CTC  AGA  AGC  CTG  ACA  AAT  GAG  GAC  TCT  GCG  GTC  TAT  TTC  TGT       288
Met  Glu  Leu  Arg  Ser  Leu  Thr  Asn  Glu  Asp  Ser  Ala  Val  Tyr  Phe  Cys
                    85                  90                            95

ACA  AAA  GAG  GAA  TAT  GAT  TAC  GAC  ACC  CTG  GAC  TAC  TGG  GGT  CAA  GGA       336
Thr  Lys  Glu  Glu  Tyr  Asp  Tyr  Asp  Thr  Leu  Asp  Tyr  Trp  Gly  Gln  Gly
               100                      105                      110

ACC  TCA  GTC  ACC  GTC  TCC  TCA                                                    357
Thr  Ser  Val  Thr  Val  Ser  Ser
          115
```

( 2 ) INFORMATION FOR SEQ ID NO: 32:

( i ) SEQUENCE CHARACTERISTICS:
    ( A ) LENGTH:366 base pairs
    ( B ) TYPE:nucleic acid
    ( C ) STRANDEDNESS:double
    ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
    ( A ) ORGANISM:mouse ( i x ) FEATURE:
    ( A ) NAME/KEY:Idio 20 H chain variable ( x i ) SEQUENCE DESCRIPTION:SEQ ID NO: 32:

```
GAG  GTG  AAG  CTG  GTG  GAG  TCT  GGA  GGA  GGC  TTG  GTA  CAG  CCT  GGG  GGT        48
Glu  Val  Lys  Leu  Val  Glu  Ser  Gly  Gly  Gly  Leu  Val  Gln  Pro  Gly  Gly
                    5                   10                            15

TCT  CTC  AGA  CTC  TCC  TGT  GCA  ACT  TCT  GGG  TTA  ACC  TTC  ACT  GAT  TAC        96
Ser  Leu  Arg  Leu  Ser  Cys  Ala  Thr  Ser  Gly  Leu  Thr  Phe  Thr  Asp  Tyr
               20                       25                            30

TAC  ATG  AAC  TGG  GTC  CGC  CAG  CCT  CCA  GGA  AAG  GAA  CTT  GAA  TGG  TTG       144
Tyr  Met  Asn  Trp  Val  Arg  Gln  Pro  Pro  Gly  Lys  Glu  Leu  Glu  Trp  Leu
          35                       40                       45

GGT  TTT  ATT  AGA  AAC  AAA  GCT  AAT  CTT  TAC  ACA  ACA  GAC  TAC  AGT  GCA       192
Gly  Phe  Ile  Arg  Asn  Lys  Ala  Asn  Leu  Tyr  Thr  Thr  Asp  Tyr  Ser  Ala
     50                       55                       60

TCT  GTG  AAG  GGT  CGG  TTC  ACC  ATC  TCC  AGA  CAT  AAT  CCC  CAA  AGC  ATC       240
Ser  Val  Lys  Gly  Arg  Phe  Thr  Ile  Ser  Arg  Asp  Asn  Pro  Gln  Ser  Ile
65                  70                       75                           80

CTC  TAT  CTT  CAA  ATG  AAC  ACC  CTG  ACA  ACT  GAG  GAC  AGT  GCC  ACT  TAT       288
Leu  Tyr  Leu  Gln  Met  Asn  Thr  Leu  Thr  Thr  Glu  Asp  Ser  Ala  Thr  Tyr
                    85                  90                            95

TAC  TGT  GCA  AGA  GAT  AGG  GGG  GGG  AGG  GAC  TGG  TAC  TTC  GAT  GTC  TGG       336
Tyr  Cys  Ala  Arg  Asp  Arg  Gly  Gly  Arg  Asp  Trp  Tyr  Phe  Asp  Val  Trp
               100                      105                      110

GGC  GCA  GGG  ACC  ACG  GTC  ACC  GTC  TCC  TCA                                     366
Gly  Ala  Gly  Thr  Thr  Val  Thr  Val  Ser  Ser
          115                      120
```

( 2 ) INFORMATION FOR SEQ ID NO: 33:

( i ) SEQUENCE CHARACTERISTICS:
    ( A ) LENGTH:366 base pairs
    ( B ) TYPE:nucleic acid
    ( C ) STRANDEDNESS:double
    ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
　　　　( A ) ORGANISM:mouse ( i x ) FEATURE:
　　　　( A ) NAME/KEY:Idio 27 H chain variable ( x i ) SEQUENCE DESCRIPTION:SEQ ID NO: 33:

```
GAG GTG AAG CTG GTG GAG TCT GGA GGA GGC TTG GTA CAG CCT GGG GGT     48
Glu Val Lys Leu Val Glu Ser Gly Gly Gly Leu Val Gln Pro Gly Gly
 5              10                      15

TCT CTG AGA CTC TCC TGT GCA ACT TCT GGG TTC ACC TTC ACT GAT TAC     96
Ser Leu Arg Leu Ser Cys Ala Thr Ser Gly Phe Thr Phe Thr Asp Tyr
20              25                      30

TAC ATG AAC TGG GTC CGC CAG CCT CCA GGA AAG GCA CTT GAG TGG TTG    144
Tyr Met Asn Trp Val Arg Gln Pro Pro Gly Lys Ala Leu Glu Trp Leu
35              40                      45

GGT TTT ATT AGA AAC AAA GCT AAT TAT TAC ACA ACA GAG TAC AGT GCA    192
Gly Phe Ile Arg Asn Lys Ala Asn Tyr Tyr Thr Thr Glu Tyr Ser Ala
50              55                      60

TCT GTG AAG GGT CGG TTC ACC ATC TCC AGA GAT AAT TCC CAA AGC ATC    240
Ser Val Lys Gly Arg Phe Thr Ile Ser Arg Asp Asn Ser Gln Ser Ile
65              70                      75                  80

CTC TAT CTT CAA ATG AAC ACC CTG AGA GCT GAG GAC AGT GCC ACT TAT    288
Leu Tyr Leu Gln Met Asn Thr Leu Arg Ala Glu Asp Ser Ala Thr Tyr
85              90                      95

TAC TGT GCA AGA GAT GGG TTC CTA CGG GAC TGG TAC TTC GAT GTC TGG    336
Tyr Cys Ala Arg Asp Gly Phe Leu Arg Asp Trp Tyr Phe Asp Val Trp
100             105                     110

GGC GCA GGG ACC ACG GTC ACC GTC TCC TCA                            366
Gly Ala Gly Thr Thr Val Thr Val Ser Ser
115             120
```

( 2 ) INFORMATION FOR SEQ ID NO: 34:

( i ) SEQUENCE CHARACTERISTICS:
　　　　　　　( A ) LENGTH:363 base pairs
　　　　　　　( B ) TYPE:nucleic acid
　　　　　　　( C ) STRANDEDNESS:double
　　　　　　　( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
　　　　　　　( A ) ORGANISM:mouse ( i x ) FEATURE:
　　　　　　　( A ) NAME/KEY:Idio 33 H chain variable ( x i ) SEQUENCE DESCRIPTION:SEQ ID NO: 34:

```
GAG GTT CAG CTC CAG CAG TCT GGG GCT GAA CTG GCA AGA CCT GGG GCT     48
Glu Val Gln Leu Gln Gln Ser Gly Ala Glu Leu Ala Arg Pro Gly Ala
 5              10                      15

TCA GTG AAC TTG TCC TGC AAG GCT TCT GGC TAC ACC TTT ACT AAC TAC     96
Ser Val Asn Leu Ser Cys Lys Ala Ser Gly Tyr Thr Phe Thr Asn Tyr
20              25                      30

TGG ATG CAG TGG GTA AAA CAG AGG CCT GGA CAG GGT CTG GAA TGG ATT    144
Trp Met Gln Trp Val Lys Gln Arg Pro Gly Gln Gly Leu Glu Trp Ile
35              40                      45
```

```
GGG  GCT  ATT  TAT  CCT  GGA  GAT  GGT  GAT  ACT  AGG  TAC  ACT  CAG  AAG  TTC         192
Gly  Ala  Ile  Tyr  Pro  Gly  Asp  Gly  Asp  Thr  Arg  Tyr  Thr  Gln  Lys  Phe
          50                      55                           60

AAG  GGC  AAG  GCC  ACA  TTG  ACT  GCA  GCT  AAA  TCC  TCC  AGC  ACA  GCC  TAC         240
Lys  Gly  Lys  Ala  Thr  Leu  Thr  Ala  Ala  Lys  Ser  Ser  Ser  Thr  Ala  Tyr
 65                      70                      75                           80

ATG  CAA  CTC  AGC  AGC  TTG  GCA  TCT  GAG  GAC  TCT  GCG  GTC  TAT  TAC  TGT         288
Met  Gln  Leu  Ser  Ser  Leu  Ala  Ser  Glu  Asp  Ser  Ala  Val  Tyr  Tyr  Cys
                    85                           90                      95

GCA  AGA  TCG  GGC  TAC  TAT  GGT  AGC  TTC  GTT  GGG  TTT  GCT  TAC  TGG  GGC         336
Ala  Arg  Ser  Gly  Tyr  Tyr  Gly  Ser  Phe  Val  Gly  Phe  Ala  Tyr  Trp  Gly
               100                           105                    110

CAA  GGG  ACT  CTG  GTC  ACT  GTC  TCT  GCA                                            363
Gln  Gly  Thr  Leu  Val  Thr  Val  Ser  Ala
          115                      120
```

( 2 ) INFORMATION FOR SEQ ID NO: 35:

( i ) SEQUENCE CHARACTERISTICS:
        ( A ) LENGTH:336 base pairs
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
        ( A ) ORGANISM:mouse ( i x ) FEATURE:
        ( A ) NAME/KEY:Idio 3 L chain ( x i ) SEQUENCE DESCRIPTION:SEQ ID NO: 35:

```
GAC  ATT  GTG  CTG  ACA  CAG  TCT  CCT  GCT  TCC  TTA  GCT  GTA  TCT  CCT  CTG         48
Asp  Ile  Val  Leu  Thr  Gln  Ser  Pro  Ala  Ser  Leu  Ala  Val  Ser  Pro  Leu
                     5                       10                           15

GGG  CAG  AGG  GCC  ACC  ATC  TCA  TAC  AGG  GCC  AGC  AAA  AGT  GTG  CAG  TTA         96
Gly  Gln  Arg  Ala  Thr  Ile  Ser  Tyr  Arg  Ala  Ser  Lys  Ser  Val  Gln  Leu
               20                       25                           30

CAT  CTG  GCT  ATA  GTT  TAT  ATG  CAC  TGG  AAC  CAA  CAG  AAA  CCA  GGA  CAG        144
His  Leu  Ala  Ile  Val  Tyr  Met  His  Trp  Asn  Gln  Gln  Lys  Pro  Gly  Gln
               35                       40                      45

CCA  CCC  AGA  CTC  CTC  ATC  TAT  CTT  GTA  TCC  AAC  CTA  GAA  TCT  GGG  GTC        192
Pro  Pro  Arg  Leu  Leu  Ile  Tyr  Leu  Val  Ser  Asn  Leu  Glu  Ser  Gly  Val
          50                      55                      60

CCT  GCC  AGG  TTC  AGT  GGC  AGT  GGG  TCT  GGG  ACA  GAC  TTC  ACC  CTC  AAC        240
Pro  Ala  Arg  Phe  Ser  Gly  Ser  Gly  Ser  Gly  Thr  Asp  Phe  Thr  Leu  Asn
 65                      70                      75                           80

ATC  CAT  CCT  GTG  GAG  GAG  GAG  GAT  GCT  GCA  ACC  TAT  TAC  TGT  CAG  CAC        288
Ile  His  Pro  Val  Glu  Glu  Glu  Asp  Ala  Ala  Thr  Tyr  Tyr  Cys  Gln  His
                    85                           90                      95

ATT  AGG  GTA  GCT  TAC  ACG  TTC  GGA  GGG  GGG  ACC  AAG  CTG  GAA  ATA  AAA        336
Ile  Arg  Val  Ala  Tyr  Thr  Phe  Gly  Gly  Gly  Thr  Lys  Leu  Glu  Ile  Lys
               100                      105                     110
```

( 2 ) INFORMATION FOR SEQ ID NO: 36:

( i ) SEQUENCE CHARACTERISTICS:
        ( A ) LENGTH:330 base pairs
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
  ( A ) ORGANISM:mouse ( i x ) FEATURE:
  ( A ) NAME/KEY:Idio 17 L chain variable ( x i ) SEQUENCE DESCRIPTION:SEQ ID NO: 36:

| GAC | ATT | GTG | CTG | ACA | CAG | TCT | CCT | GCT | TCC | TTA | GCT | GTA | TCT | CTG | GGG | 48 |
|---|---|---|---|---|---|---|---|---|---|---|---|---|---|---|---|---|
| Asp | Ile | Val | Leu | Thr | Gln | Ser | Pro | Ala | Ser | Leu | Ala | Val | Ser | Leu | Gly | |
| | | | | 5 | | | | | 10 | | | | | 15 | | |

| CAG | AGG | GCC | TCC | ATC | TCA | TAC | AGG | GCC | AGC | AAA | AGT | GTC | AGT | ACA | TCT | 96 |
|---|---|---|---|---|---|---|---|---|---|---|---|---|---|---|---|---|
| Gln | Arg | Ala | Ser | Ile | Ser | Tyr | Arg | Ala | Ser | Lys | Ser | Val | Ser | Thr | Ser | |
| | | | | 20 | | | | | 25 | | | | | 30 | | |

| GGC | TAT | AGT | TAT | ATG | CAC | TGG | AAC | CAA | CAG | AAA | CCA | GGA | CAG | CCA | CCC | 144 |
|---|---|---|---|---|---|---|---|---|---|---|---|---|---|---|---|---|
| Gly | Tyr | Ser | Tyr | Met | His | Trp | Asn | Gln | Gln | Lys | Pro | Gly | Gln | Pro | Pro | |
| | | | 35 | | | | | 40 | | | | | 45 | | | |

| AGA | CTC | CTC | ATC | TAT | CTT | GTA | TCC | AAC | CTA | GAA | TCT | GGG | GTC | CCT | GCC | 192 |
|---|---|---|---|---|---|---|---|---|---|---|---|---|---|---|---|---|
| Arg | Leu | Leu | Ile | Tyr | Leu | Val | Ser | Asn | Leu | Glu | Ser | Gly | Val | Pro | Ala | |
| | | 50 | | | | | 55 | | | | | 60 | | | | |

| AGG | TTC | AGT | GGC | AGT | GGG | TCT | GGG | ACA | GAC | TTC | ACC | CTC | AAC | ATC | CAT | 240 |
|---|---|---|---|---|---|---|---|---|---|---|---|---|---|---|---|---|
| Arg | Phe | Ser | Gly | Ser | Gly | Ser | Gly | Thr | Asp | Phe | Thr | Leu | Asn | Ile | His | |
| 65 | | | | | 70 | | | | | 75 | | | | | 80 | |

| CCT | GTG | GAG | GAG | GAG | GAT | GCT | GCA | ACC | TAT | TAC | TGT | CAG | CAC | ATT | AGG | 288 |
|---|---|---|---|---|---|---|---|---|---|---|---|---|---|---|---|---|
| Pro | Val | Glu | Glu | Glu | Asp | Ala | Ala | Thr | Tyr | Tyr | Cys | Gln | His | Ile | Arg | |
| | | | | 85 | | | | | 90 | | | | | 95 | | |

| GGA | GCT | TAC | ACG | TTC | GGA | GGG | GGG | ACC | AAG | CTG | GAA | ATA | AAA | | | 330 |
|---|---|---|---|---|---|---|---|---|---|---|---|---|---|---|---|---|
| Gly | Ala | Tyr | Thr | Phe | Gly | Gly | Gly | Thr | Lys | Leu | Glu | Ile | Lys | | | |
| | | | 100 | | | | | 105 | | | | | 110 | | | |

( 2 ) INFORMATION FOR SEQ ID NO: 37:

( i ) SEQUENCE CHARACTERISTICS:
  ( A ) LENGTH:330 base pairs
  ( B ) TYPE:nucleic acid
  ( C ) STRANDEDNESS:double
  ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
  ( A ) ORGANISM:mouse ( i x ) FEATURE:
  ( A ) NAME/KEY:Idio 20 L chain ( x i ) SEQUENCE DESCRIPTION:SEQ ID NO: 37:

| GAC | ATT | GTG | CTG | ACA | CAG | TCT | CCT | GCT | TCC | TTA | GCT | GTA | TCT | CTG | GGG | 48 |
|---|---|---|---|---|---|---|---|---|---|---|---|---|---|---|---|---|
| Asp | Ile | Val | Leu | Thr | Gln | Ser | Pro | Ala | Ser | Leu | Ala | Val | Ser | Leu | Gly | |
| | | | | 5 | | | | | 10 | | | | | 15 | | |

| CAG | AGG | GCC | ACC | ATC | TCA | TAC | AGG | GCC | AGC | AAA | AGT | GTC | AGT | ACA | TCT | 96 |
|---|---|---|---|---|---|---|---|---|---|---|---|---|---|---|---|---|
| Gln | Arg | Ala | Thr | Ile | Ser | Tyr | Arg | Ala | Ser | Lys | Ser | Val | Ser | Thr | Ser | |
| | | | | 20 | | | | | 25 | | | | | 30 | | |

| GGC | TAT | AGT | TAT | ATG | CAC | TGG | AAC | CAA | CAG | AGA | CCA | GGA | CAG | CCA | CCC | 144 |
|---|---|---|---|---|---|---|---|---|---|---|---|---|---|---|---|---|
| Gly | Tyr | Ser | Tyr | Met | His | Trp | Asn | Gln | Gln | Arg | Pro | Gly | Gln | Pro | Pro | |
| | | | 35 | | | | | 40 | | | | | 45 | | | |

| AGA | CTC | CTC | ATC | TAT | CTT | GTA | TCC | AAC | CTA | GAC | TCT | GGG | GTC | CCT | GCC | 192 |
|---|---|---|---|---|---|---|---|---|---|---|---|---|---|---|---|---|
| Arg | Leu | Leu | Ile | Tyr | Leu | Val | Ser | Asn | Leu | Asp | Ser | Gly | Val | Pro | Ala | |

|     |     |     |     |     |     |     |     |     |     |     |     |     |     |     |     |     |
|---|---|---|---|---|---|---|---|---|---|---|---|---|---|---|---|---|
|     |     |     | 50  |     |     |     | 55  |     |     |     | 60  |     |     |     |     |     |
| AGG | TTC | AGT | GGC | AGT | GGG | TCT | GGG | ACA | GAC | TTC | ACC | CTC | AAC | ATC | CAT | 240 |
| Arg | Phe | Ser | Gly | Ser | Gly | Ser | Gly | Thr | Asp | Phe | Thr | Leu | Asn | Ile | His |     |
| 65  |     |     |     |     | 70  |     |     |     |     | 75  |     |     |     |     | 80  |     |
| CCT | GTG | GAG | GAG | GAG | GAT | GCT | GCA | ACC | TAT | TAC | TGT | CAG | CAC | ATT | GAG | 288 |
| Pro | Val | Glu | Glu | Glu | Asp | Ala | Ala | Thr | Tyr | Tyr | Cys | Gln | His | Ile | Glu |     |
|     |     |     |     | 85  |     |     |     |     | 90  |     |     |     |     | 95  |     |     |
| GGA | GCT | TAC | ACG | TTC | GGA | GGG | GGG | ACC | AAG | CTG | GAA | ATA | AAA |     |     | 330 |
| Gly | Ala | Tyr | Thr | Phe | Gly | Gly | Gly | Thr | Lys | Leu | Glu | Ile | Lys |     |     |     |
|     |     |     | 100 |     |     |     |     | 105 |     |     |     |     | 110 |     |     |     |

( 2 ) INFORMATION FOR SEQ ID NO: 38:

( i ) SEQUENCE CHARACTERISTICS:
        ( A ) LENGTH:321 nucleotides
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
        ( A ) ORGANISM:mouse ( i x ) FEATURE:
        ( A ) NAME/KEY:Idio 27 L chain ( x i ) SEQUENCE DESCRIPTION:SEQ ID NO: 38:

|     |     |     |     |     |     |     |     |     |     |     |     |     |     |     |     |     |
|---|---|---|---|---|---|---|---|---|---|---|---|---|---|---|---|---|
| GAC | ATT | GTG | ATG | ACC | CAG | TCT | CAC | AAA | TTC | ATG | TCC | ACA | TCA | GTA | GGA | 48 |
| Asp | Ile | Val | Met | Thr | Gln | Ser | His | Lys | Phe | Met | Ser | Thr | Ser | Val | Gly |     |
|     |     |     |     | 5   |     |     |     |     | 10  |     |     |     |     | 15  |     |     |
| GAC | AGG | GTC | AGT | ATC | ACC | TGC | AAG | GCC | AGT | CAG | GAT | GTG | AAT | ACT | GCT | 96 |
| Asp | Arg | Val | Ser | Ile | Thr | Cys | Lys | Ala | Ser | Gln | Asp | Val | Asn | Thr | Ala |     |
|     |     |     | 20  |     |     |     |     | 25  |     |     |     |     | 30  |     |     |     |
| GTA | GCC | TGG | TAT | CAA | CAG | AAA | CCA | GGA | CAA | TCT | CCT | AAA | CTA | CTG | CTT | 144 |
| Val | Ala | Trp | Tyr | Gln | Gln | Lys | Pro | Gly | Gln | Ser | Pro | Lys | Leu | Leu | Leu |     |
|     |     | 35  |     |     |     |     | 40  |     |     |     |     | 45  |     |     |     |     |
| TAC | TCG | GCA | TCC | TAC | CGG | TAC | ACT | GGA | GTC | CCT | GAT | CAC | TTC | ACT | GGC | 192 |
| Tyr | Ser | Ala | Ser | Tyr | Arg | Tyr | Thr | Gly | Val | Pro | Asp | His | Phe | Thr | Gly |     |
|     | 50  |     |     |     |     | 55  |     |     |     |     | 60  |     |     |     |     |     |
| AGT | GGA | TCT | GGG | ACG | GAT | TTC | ACT | TTC | ACC | ATC | AGC | GGT | GTG | CAG | GCT | 240 |
| Ser | Gly | Ser | Gly | Thr | Asp | Phe | Thr | Phe | Thr | Ile | Ser | Gly | Val | Gln | Ala |     |
| 65  |     |     |     |     | 70  |     |     |     |     | 75  |     |     |     |     | 80  |     |
| GAA | GAC | CTG | GCA | GTT | TAT | TAC | TGT | CAG | CAA | CAT | TAT | AGT | CCT | CCT | CTC | 288 |
| Glu | Asp | Leu | Ala | Val | Tyr | Tyr | Cys | Gln | Gln | His | Tyr | Ser | Pro | Pro | Leu |     |
|     |     |     |     | 85  |     |     |     |     | 90  |     |     |     |     | 95  |     |     |
| ACG | TTC | GGT | GCT | GGG | ACC | AAG | CTG | GAA | CTG | AAA |     |     |     |     |     | 321 |
| Thr | Phe | Gly | Ala | Gly | Thr | Lys | Leu | Glu | Leu | Lys |     |     |     |     |     |     |
|     |     |     | 100 |     |     |     |     | 105 |     |     |     |     |     |     |     |     |

( 2 ) INFORMATION FOR SEQ ID NO: 39:

( i ) SEQUENCE CHARACTERISTICS:
        ( A ) LENGTH:321 base pairs
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no (vi) ORIGINAL SOURCE:
  (A) ORGANISM:mouse (ix) FEATURE:
  (A) NAME/KEY:Idio 33 L chain variable (xi) SEQUENCE DESCRIPTION:SEQ ID NO: 39:

| | | | | | | | | | | | | | | | | |
|---|---|---|---|---|---|---|---|---|---|---|---|---|---|---|---|---|
| GAC | ATT | GTG | ATG | ACA | CAG | TCT | CAC | AAA | TTC | ATG | TCC | ACA | TCA | GTT | GGA | 48 |
| Asp | Ile | Val | Met | Thr | Gln | Ser | His | Lys | Phe | Met | Ser | Thr | Ser | Val | Gly | |
| | | | | 5 | | | | 10 | | | | | | 15 | | |
| GAC | AGG | GTC | ACC | ATC | ACC | TGC | AAG | GCC | AGT | CAG | GAT | GTG | ACT | ACT | GAT | 96 |
| Asp | Arg | Val | Thr | Ile | Thr | Cys | Lys | Ala | Ser | Gln | Asp | Val | Thr | Thr | Asp | |
| | | | 20 | | | | | 25 | | | | | 30 | | | |
| GTA | GCC | TGG | TAT | CAA | CAG | AAA | CCA | CGA | CAA | TCT | CCT | AAA | CTA | CTG | ATT | 144 |
| Val | Ala | Trp | Tyr | Gln | Gln | Lys | Pro | Arg | Gln | Ser | Pro | Lys | Leu | Leu | Ile | |
| | | 35 | | | | | 40 | | | | | 45 | | | | |
| TAC | TCG | GCA | TCC | TAT | CGG | TAC | ACT | GGA | GTC | CCT | GAT | CGC | TTC | ACT | GGC | 192 |
| Tyr | Ser | Ala | Ser | Tyr | Arg | Tyr | Thr | Gly | Val | Pro | Asp | Arg | Phe | Thr | Gly | |
| | 50 | | | | | 55 | | | | | 60 | | | | | |
| AGT | GGA | TCT | GGG | ACG | GAT | TTC | ACT | TTC | ACC | ATC | AGC | AGT | GTG | CAG | GCT | 240 |
| Ser | Gly | Ser | Gly | Thr | Asp | Phe | Thr | Phe | Thr | Ile | Ser | Ser | Val | Gln | Ala | |
| 65 | | | | | 70 | | | | | 75 | | | | | 80 | |
| GAA | GAC | CTG | GCA | GTT | TAT | TAC | TGT | CAG | CAA | CAT | TAT | AGT | ACT | GCG | TGG | 288 |
| Glu | Asp | Leu | Ala | Val | Tyr | Tyr | Cys | Gln | Gln | His | Tyr | Ser | Thr | Ala | Trp | |
| | | | | 85 | | | | | 90 | | | | | 95 | | |
| ACG | TTC | GGT | GGT | GGC | ACC | AAG | CTG | GAA | ATC | AAA | | | | | | 321 |
| Thr | Phe | Gly | Gly | Gly | Thr | Lys | Leu | Glu | Ile | Lys | | | | | | |
| | | | 100 | | | | | 105 | | | | | | | | |

(2) INFORMATION FOR SEQ ID NO: 40:

(i) SEQUENCE CHARACTERISTICS:
    (A) LENGTH:399 base pairs
    (B) TYPE:nucleic acid
    (C) STRANDEDNESS:double
    (D) TOPOLOGY:linear (ii) MOLECULE TYPE:mRNA (iii) HYPOTHETICAL:no (iv) ANTI-SENSE:no (vi) ORIGINAL SOURCE:
    (A) ORGANISM:mouse (ix) FEATURE:
    (A) NAME/KEY:Clone 3GB1

(xi) SEQUENCE DESCRIPTION:SEQ ID NO:40:

| | | | | | | | | | | | | | | | | |
|---|---|---|---|---|---|---|---|---|---|---|---|---|---|---|---|---|
| CTG | TCG | GTA | ACT | TCA | GGG | GTC | TAC | TCA | GAG | GTT | CAG | CTC | GAG | CAG | TCT | 48 |
| Leu | Ser | Val | Thr | Ser | Gly | Val | Tyr | Ser | Glu | Val | Gln | Leu | Gln | Gln | Ser | |
| | | | | -5 | | | | | 1 | | | | | 5 | | |
| GGG | ACT | GTG | CTG | GCA | AGG | CCT | GGG | GCT | TCA | GTG | AAG | ATG | TCC | TGC | AAG | 96 |
| Gly | Thr | Val | Leu | Ala | Arg | Pro | Gly | Ala | Ser | Val | Lys | Met | Ser | Cys | Lys | |
| | | 10 | | | | | 15 | | | | | 20 | | | | |
| GCT | TCG | GGC | TAC | ACC | TTT | AAC | AGC | TAC | TGG | ATG | CAC | TGG | GTA | AAA | CAG | 144 |
| Ala | Ser | Gly | Tyr | Thr | Phe | Asn | Ser | Tyr | Trp | Met | His | Trp | Val | Lys | Gln | |
| | 25 | | | | | 30 | | | | | 35 | | | | | |
| AGG | CCT | GGA | CAG | GGT | CTG | GAA | TGG | ATT | GGC | GCG | ATT | TAT | CCT | GGA | AAT | 192 |
| Arg | Pro | Gly | Gln | Gly | Leu | Glu | Trp | Ile | Gly | Ala | Ile | Tyr | Pro | Gly | Asn | |
| 40 | | | | | 45 | | | | | 50 | | | | | 55 | |
| AGT | GAT | ATT | AGC | TAC | AGC | CAG | AAC | TTT | AAG | GAC | AGG | GCC | AAA | CTG | ACT | 240 |
| Ser | Asp | Ile | Ser | Tyr | Ser | Gln | Asn | Phe | Lys | Asp | Arg | Ala | Lys | Leu | Thr | |
| | | | | 60 | | | | | 65 | | | | | 70 | | |
| GCC | GTC | ACA | TCC | ACC | AGC | ACT | GCC | TAC | ATG | GAA | CTC | AGA | AGC | CTG | ACA | 288 |

```
Ala Val Thr Ser Thr Ser Thr Ala Tyr Met Glu Leu Arg Ser Leu Thr
            75              80                      85

AAT GAG GAC TCT GCG GTC TAT TTC TGT ACA AAA GAG GAA TAT GAT TAC        336
Asn Glu Asp Ser Ala Val Tyr Phe Cys Thr Lys Glu Glu Tyr Asp Tyr
        90                  95                  100

GAC ACC CTG GAC TAC TGG GGT CAA GGA ACC TCA GTC ACC GTC TCC TCA        384
Asp Thr Leu Asp Tyr Trp Gly Gln Gly Thr Ser Val Thr Val Ser Ser
    105                 110                 115

GCC AAA ACG ACA CCC                                                    399
Ala Lys Thr Thr Pro
120
```

( 2 ) INFORMATION FOR SEQ ID NO: 41:

( i ) SEQUENCE CHARACTERISTICS:
        ( A ) LENGTH:402 base pairs
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
        ( A ) ORGANISM:mouse ( i x ) FEATURE:
        ( A ) NAME/KEY:Clone 17GB7

( x i ) SEQUENCE DESCRIPTION:SEQ ID NO: 41:

```
ATT GTG TCG GTA ACT TCA GGG GTC TAC TCA GAG GTT CAG CTC GAG CAG         48
Ile Leu Ser Val Thr Ser Gly Val Tyr Ser Glu Val Gln Leu Glu Gln
-10                 -5                  1               5

TCT GGG ACT GTG CTG GCA AGG CCT GGG GCT TCA GTG AAG ATG TCC TGC         96
Ser Gly Thr Val Leu Ala Arg Pro Gly Ala Ser Val Lys Met Ser Cys
            10                  15                  20

AAG GCT TCG GGC TAC ACC TTT AAC AGC TAC TGG ATG CAC TGG GTA AAA        144
Lys Ala Ser Gly Tyr Thr Phe Asn Ser Tyr Trp Met His Trp Val Lys
        25                  30                  35

CAG AGG CCT GGA CAG GGT CTG GAA TGG ATT GGC GCG ATT TAT CCT GGA        192
Gln Arg Pro Gly Gln Gly Leu Glu Trp Ile Gly Ala Ile Tyr Pro Gly
    40                  45                  50

AAT AGT GAT ATT AGC TAC AGC CAG AAC TTT AAG GAC AGG GCC AAA CTG        240
Asn Ser Asp Ile Ser Tyr Ser Gln Asn Phe Lys Asp Arg Ala Lys Leu
55                  60                  65                      70

ACT GCC GTC ACA TCC ACC AGC ACT GCC TAC ATG GAA CTC AGA AGC CTG        288
Thr Ala Val Thr Ser Thr Ser Thr Ala Tyr Met Glu Leu Arg Ser Leu
            75                  80                      85

ACA AAT GAG GAC TCT GCG GTC TAT TTC TGT ACA AAA GAG GAA TAT GAT        336
Thr Asn Glu Asp Ser Ala Val Tyr Phe Cys Thr Lys Glu Glu Tyr Asp
            90                  95                  100

TAC GAC ACC CTG GAC TAC TGG GGT CAA GGA ACC TCA GTC ACC GTC TCC        384
Tyr Asp Thr Leu Asp Tyr Trp Gly Gln Gly Thr Ser Val Thr Val Ser
        105                 110                 115

TCA GCC AAA ACG ACA CCC                                                402
Ser Ala Lys Thr Thr Pro
        120
```

( 2 ) INFORMATION FOR SEQ ID NO: 42:

( i ) SEQUENCE CHARACTERISTICS:
        ( A ) LENGTH:438 nucleotides
        ( B ) TYPE:nucleic acid ( C ) STRANDEDNESS:double
( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
 ( A ) ORGANISM:mouse ( i x ) FEATURE:
 ( A ) NAME/KEY:Clone 20GA2

( x i ) SEQUENCE DESCRIPTION:SEQ ID NO:42:

| ATG | GAG | TTC | GGG | CTA | AAC | TGG | GTT | TTC | CTT | GTA | ACA | CTT | TTA | AAT | GGT | 48 |
| Met | Glu | Phe | Gly | Leu | Asn | Trp | Val | Phe | Leu | Val | Thr | Leu | Leu | Asn | Gly | |
| | | | | -15 | | | | | -10 | | | | | -5 | | |
| ATC | CAG | TGT | GAG | GTG | AAG | CTG | GTG | GAG | TCT | GGA | GGA | GGC | TTG | GTA | CAG | 96 |
| Ile | Gln | Cys | Glu | Val | Lys | Leu | Val | Glu | Ser | Gly | Gly | Gly | Leu | Val | Gln | |
| | | | 1 | | | | 5 | | | | | | 10 | | | |
| CCT | GGG | GGT | TCT | CTC | AGA | CTC | TCC | TGT | GCA | ACT | TCT | GGG | TTA | ACC | TTC | 144 |
| Pro | Gly | Gly | Ser | Leu | Arg | Leu | Ser | Cys | Ala | Thr | Ser | Gly | Leu | Thr | Phe | |
| | 15 | | | | 20 | | | | | 25 | | | | | | |
| ACT | GAT | TAC | TAC | ATG | AAC | TGG | GTC | CGC | CAG | CCT | CCA | GGA | AAG | GAA | CTT | 192 |
| Thr | Asp | Tyr | Tyr | Met | Asn | Trp | Val | Arg | Gln | Pro | Pro | Gly | Lys | Glu | Leu | |
| 30 | | | | 35 | | | | | 40 | | | | | | 45 | |
| GAA | TGG | TTG | GGT | TTT | ATT | AGA | AAC | AAA | GCT | AAT | CTT | TAC | ACA | ACA | GAC | 240 |
| Glu | Trp | Leu | Gly | Phe | Ile | Arg | Asn | Lys | Ala | Asn | Leu | Tyr | Thr | Thr | Asp | |
| | | | | 50 | | | | | 55 | | | | | 60 | | |
| TAC | AGT | GCA | TCT | GTG | AAG | GGT | CGG | TTC | ACC | ATC | TCC | AGA | CAT | AAT | CCC | 288 |
| Tyr | Ser | Ala | Ser | Val | Lys | Gly | Arg | Phe | Thr | Ile | Ser | Arg | Asp | Asn | Pro | |
| | | | 65 | | | | | 70 | | | | | 75 | | | |
| CAA | AGC | ATC | CTC | TAT | CTT | CAA | ATG | AAC | ACC | CTG | ACA | ACT | GAG | GAC | AGT | 336 |
| Gln | Ser | Ile | Leu | Tyr | Leu | Gln | Met | Asn | Thr | Leu | Thr | Thr | Glu | Asp | Ser | |
| | | 80 | | | | | 85 | | | | | 90 | | | | |
| GCC | ACT | TAT | TAC | TGT | GCA | AGA | GAT | AGG | GGG | GGG | AGG | GAC | TGG | TAC | TTC | 384 |
| Ala | Thr | Tyr | Tyr | Cys | Ala | Arg | Asp | Arg | Gly | Gly | Arg | Asp | Trp | Tyr | Phe | |
| | 95 | | | | 100 | | | | | 105 | | | | | | |
| GAT | GTC | TGG | GGC | GCA | GGG | ACC | ACG | GTC | ACC | GTC | TCC | TCA | GCC | AAA | ACG | 432 |
| Asp | Val | Trp | Gly | Ala | Gly | Thr | Thr | Val | Thr | Val | Ser | Ser | Ala | Lys | Thr | |
| 110 | | | | 115 | | | | | 120 | | | | | 125 | | |
| ACA | CCC | | | | | | | | | | | | | | | 438 |
| Thr | Pro | | | | | | | | | | | | | | | |

( 2 ) INFORMATION FOR SEQ ID NO: 43:

( i ) SEQUENCE CHARACTERISTICS:
 ( A ) LENGTH:411 base pairs
 ( B ) TYPE:nucleic acid
 ( C ) STRANDEDNESS:double
 ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
 ( A ) ORGANISM:

( i x ) FEATURE:
 ( A ) NAME/KEY:Clone 27GA5

( x i ) SEQUENCE DESCRIPTION:SEQ ID NO: 43:

CTT GTA ACA CGT TTA AAT GGT ATC CAG TGT GAG GTG AAG CTG GTG GAG    48

```
Leu  Val  Thr  Arg  Leu  Asn  Gly  Ile  Gln  Cys  Glu  Val  Lys  Leu  Val  Glu
-10                   -5                      1                    5
```

| | | | | | | | | | | | | | | | | |
|---|---|---|---|---|---|---|---|---|---|---|---|---|---|---|---|---|
| TCT | GGA | GGA | GGC | TTG | GTA | CAG | CCT | GGG | GGT | TCT | CTG | AGA | CTC | TCC | TGT | 96 |
| Ser | Gly | Gly | Gly | Leu | Val | Gln | Pro | Gly | Gly | Ser | Leu | Arg | Leu | Ser | Cys | |
| | | | 10 | | | | | 15 | | | | | 20 | | | |
| GCA | ACT | TCT | GGG | TTC | ACC | TTC | ACT | GAT | TAC | TAC | ATG | AAC | TGG | GTC | CGC | 144 |
| Ala | Thr | Ser | Gly | Phe | Thr | Phe | Thr | Asp | Tyr | Tyr | Met | Asn | Trp | Val | Arg | |
| | | 25 | | | | | 30 | | | | | 35 | | | | |
| CAG | CCT | CCA | GGA | AAG | GCA | CTT | GAG | TGG | TTG | GGT | TTT | ATT | AGA | AAC | AAA | 192 |
| Gln | Pro | Pro | Gly | Lys | Ala | Leu | Glu | Trp | Leu | Gly | Phe | Ile | Arg | Asn | Lys | |
| | 40 | | | | | 45 | | | | | 50 | | | | | |
| GCT | AAT | TAT | TAC | ACA | ACA | GAG | TAC | AGT | GCA | TCT | GTG | AAG | GGT | CGG | TTC | 240 |
| Ala | Asn | Tyr | Tyr | Thr | Thr | Glu | Tyr | Ser | Ala | Ser | Val | Lys | Gly | Arg | Phe | |
| 55 | | | | | 60 | | | | | 65 | | | | | 70 | |
| ACC | ATC | TCC | AGA | GAT | AAT | TCC | CAA | AGC | ATC | CTC | TAT | CTT | CAA | ATG | AAC | 288 |
| Thr | Ile | Ser | Arg | Asp | Asn | Ser | Gln | Ser | Ile | Leu | Gln | Met | Asn | Thr | Leu | |
| | | | | 75 | | | | | 80 | | | | | 85 | | |
| ACC | CTG | AGA | GCT | GAG | GAC | AGT | GCC | ACT | TAT | TAC | TGT | GCA | AGA | GAT | GGG | 336 |
| Thr | Leu | Arg | Ala | Glu | Asp | Ser | Ala | Thr | Tyr | Tyr | Cys | Ala | Arg | Asp | Gly | |
| | | | 90 | | | | | 95 | | | | | 100 | | | |
| TTC | CTA | CGG | GAC | TGG | TAC | TTC | GAT | GTC | TGG | GGC | GCA | GGG | ACC | ACG | GTC | 384 |
| Phe | Leu | Arg | Asp | Trp | Tyr | Phe | Asp | Val | Trp | Gly | Ala | Gly | Thr | Thr | Val | |
| | | 105 | | | | | 110 | | | | | 115 | | | | |
| ACC | GTC | TCC | TCA | GCC | AAA | ACG | ACA | CCC | | | | | | | | 411 |
| Thr | Val | Ser | Ser | Ala | Lys | Thr | Thr | Pro | | | | | | | | |
| | 120 | | | | | 125 | | | | | | | | | | |

( 2 ) INFORMATION FOR SEQ ID NO: 44:

( i ) SEQUENCE CHARACTERISTICS:
        ( A ) LENGTH:354 base pairs
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:mouse
        ( A ) ORGANISM:

( i x ) FEATURE:
        ( A ) NAME/KEY:Clone 3KB11

( x i ) SEQUENCE DESCRIPTION:SEQ ID NO:44:

| | | | | | | | | | | | | | | | | |
|---|---|---|---|---|---|---|---|---|---|---|---|---|---|---|---|---|
| GAC | ATT | GTG | CTG | ACA | CAG | TCT | CCT | GCT | TCC | TTA | GCT | GTA | TCT | CCT | CTG | 48 |
| Asp | Ile | Val | Leu | Thr | Gln | Ser | Pro | Ala | Ser | Leu | Ala | Val | Ser | Pro | Leu | |
| | | | | 5 | | | | | 10 | | | | | 15 | | |
| GGG | CAG | AGG | GCC | ACC | ATC | TCA | TAC | AGG | GCC | AGC | AAA | AGT | GTG | CAG | TTA | 96 |
| Gly | Gln | Arg | Ala | Thr | Ile | Ser | Tyr | Arg | Ala | Ser | Lys | Ser | Val | Gln | Leu | |
| | | | 20 | | | | | 25 | | | | | 30 | | | |
| CAT | CTG | GCT | ATA | GTT | TAT | ATG | CAC | TGG | AAC | CAA | CAG | AAA | CCA | GGA | CAG | 144 |
| His | Leu | Ala | Ile | Val | Tyr | Met | His | Trp | Asn | Gln | Gln | Lys | Pro | Gly | Gln | |
| | | 35 | | | | | 40 | | | | | 45 | | | | |
| CCA | CCC | AGA | CTC | CTC | ATC | TAT | CTT | GTA | TCC | AAC | CTA | GAA | TCT | GGG | GTC | 192 |
| Pro | Pro | Arg | Leu | Leu | Ile | Tyr | Leu | Val | Ser | Asn | Leu | Glu | Ser | Gly | Val | |
| | 50 | | | | | 55 | | | | | 60 | | | | | |
| CCT | GCC | AGG | TTC | AGT | GGC | AGT | GGG | TCT | GGG | ACA | GAC | TTC | ACC | CTC | AAC | 240 |
| Pro | Ala | Arg | Phe | Ser | Gly | Ser | Gly | Ser | Gly | Thr | Asp | Phe | Thr | Leu | Asn | |
| 65 | | | | | 70 | | | | | 75 | | | | | 80 | |
| ATC | CAT | CCT | GTG | GAG | GAG | GAG | GAT | GCT | GCA | ACC | TAT | TAC | TGT | CAG | CAC | 288 |
| Ile | His | Pro | Val | Glu | Glu | Glu | Asp | Ala | Ala | Thr | Tyr | Tyr | Cys | Gln | His | |

```
                              85                           90                          95
ATT AGG GTA GCT TAC ACG TTC GGA GGG GGG ACC AAG CTG GAA ATA AAA                    336
Ile Arg Val Ala Tyr Thr Phe Gly Gly Gly Thr Lys Leu Glu Ile Lys
            100                         105                     110

CGG GCT GAT GCT GCA CCA                                                            354
Arg Ala Asp Ala Ala Pro
            115
```

( 2 ) INFORMATION FOR SEQ ID NO: 45:

( i ) SEQUENCE CHARACTERISTICS:
        ( A ) LENGTH:438 base pairs
        ( B ) TYPE:nucleic acid
        ( C ) STRANDEDNESS:double
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
        ( A ) ORGANISM:mouse ( i x ) FEATURE:
        ( A ) NAME/KEY:Clone 17KB1

( x i ) SEQUENCE DESCRIPTION:SEQ ID NO: 45:

```
CTA TGG GTA CTG CTG CTC TGG GTT CCA GGT TCC ACT GGT GAC ATT GTG             48
Leu Trp Val Leu Leu Leu Trp Val Pro Gly Ser Thr Gly Asp Ile Val
            -10                         -5                       1

CTG ACA CAG TCT CCT GCT TCC TTA GCT GTA TCT CTG GGG CAG AGG GCC             96
Leu Thr Gln Ser Pro Ala Ser Leu Ala Val Ser Leu Gly Gln Arg Ala
         5                          10                      15

TCC ATC TCA TAC AGG GCC AGC AAA AGT GTC AGT ACA TCT GGC TAT AGT            144
Ser Ile Ser Tyr Arg Ala Ser Lys Ser Val Ser Thr Ser Gly Tyr Ser
 20                       25                      30                  35

TAT ATG CAC TGG AAC CAA CAG AAA CCA GGA CAG CCA CCC AGA CTC CTC            192
Tyr Met His Trp Asn Gln Gln Lys Pro Gly Gln Pro Pro Arg Leu Leu
                40                         45                        50

ATC TAT CTT GTA TCC AAC CTA GAA TCT GGG GTC CCT GCC AGG TTC AGT            240
Ile Tyr Leu Val Ser Asn Leu Glu Ser Gly Val Pro Ala Arg Phe Ser
             55                        60                      65

GGC AGT GGG TCT GGG ACA GAC TTC ACC CTC AAC ATC CAT CCT GTG GAG            288
Gly Ser Gly Ser Gly Thr Asp Phe Thr Leu Asn Ile His Pro Val Glu
            70                        75                      80

GAG GAG GAT GCT GCA ACC TAT TAC TGT CAG CAC ATT AGG GGA GCT TAC            336
Glu Glu Asp Ala Ala Thr Tyr Tyr Cys Gln His Ile Arg Gly Ala Tyr
         85                       90                      95

ACG TTC GGA GGG GGG ACC AAG CTG GAA ATA AAA CGG GCT GAT GCT GCA            384
Thr Phe Gly Gly Gly Thr Lys Leu Glu Ile Lys Arg Ala Asp Ala Ala
100                       105                     110                 115

CCA ACT GTA TCC ATC TTC CCA CCA TCC AGT AAG CTT GGG AAA CGG TTC            432
Pro Thr Val Ser Ile Phe Pro Pro Ser Ser Lys Leu Gly Lys Arg Phe
                    120                    125                 130

GCA CCG                                                                    438
Ala Pro
```

( 2 ) INFORMATION FOR SEQ ID NO: 46:

( i ) SEQUENCE CHARACTERISTICS:
        ( A ) LENGTH:417
        ( B ) TYPE:nucleic acid
        ( C ) STRANDEDNESS:double
        ( D ) TOPOLOGY:linear (i i) MOLECULE TYPE:mRNA (i i i) HYPOTHETICAL:no (i v) ANTI-SENSE:no (v i) ORIGINAL SOURCE:
    (A) ORGANISM:mouse (i x) FEATURE:
    (A) NAME/KEY:Clone 20KB1

(x i) SEQUENCE DESCRIPTION:SEQ ID NO:46:

```
GGCCGCG  GTGAGAACCG  TTGGGAATTC  ATG  GAG  ACA  GAC  ACA  CTC  CTG                    48
                                 Met  Glu  Thr  Asp  Thr  Leu  Leu
                                 -20                      -15

CTA  TGG  GTA  CTG  CTG  CTC  TGG  GTT  CCA  GGT  TCC  ACT  GGT  GAC  ATT  GTG        96
Leu  Trp  Val  Leu  Leu  Leu  Trp  Val  Pro  Gly  Ser  Thr  Gly  Asp  Ile  Val
               -10                      -5                           1

CTG  ACA  CAG  TCT  CCT  GCT  TCC  TTA  GCT  GTA  TCT  CTG  GGG  CAG  AGG  GCC       144
Leu  Thr  Gln  Ser  Pro  Ala  Ser  Leu  Ala  Val  Ser  Leu  Gly  Gln  Arg  Ala
          5                        10                           15

ACC  ATC  TCA  TAC  AGG  GCC  AGC  AAA  AGT  GTC  AGT  ACA  TCT  GGC  TAT  AGT       192
Thr  Ile  Ser  Tyr  Arg  Ala  Ser  Lys  Ser  Val  Ser  Thr  Ser  Gly  Tyr  Ser
               20                       25                      30

TAT  ATG  CAC  TGG  AAC  CAA  CAG  AGA  CCA  GGA  CAG  CCA  CCC  AGA  CTC  CTC       240
Tyr  Met  His  Trp  Asn  Gln  Gln  Arg  Pro  Gly  Gln  Pro  Pro  Arg  Leu  Leu
     35                       40                      45

ATC  TAT  CTT  GTA  TCC  AAC  CTA  GAC  TCT  GGG  GTC  CCT  GCC  AGG  TTC  AGT       288
Ile  Tyr  Leu  Val  Ser  Asn  Leu  Asp  Ser  Gly  Val  Pro  Ala  Arg  Phe  Ser
50                       55                      60                           65

GGC  AGT  GGG  TCT  GGG  ACA  GAC  TTC  ACC  CTC  AAC  ATC  CAT  CCT  GTG  GAG       336
Gly  Ser  Gly  Ser  Gly  Thr  Asp  Phe  Thr  Leu  Asn  Ile  His  Pro  Val  Glu
                    70                      75                      80

GAG  GAG  GAT  GCT  GCA  ACC  TAT  TAC  TGT  CAG  CAC  ATT  GAG  GGA  GCT  TAC       384
Glu  Glu  Asp  Ala  Ala  Thr  Tyr  Tyr  Cys  Gln  His  Ile  Glu  Gly  Ala  Tyr
               85                       90                      95

ACG  TTC  GGA  GGG  GGG  ACC  AAG  CTG  GAA  ATA  AAA                                 417
Thr  Phe  Gly  Gly  Gly  Thr  Lys  Leu  Glu  Ile  Lys
          100                      105
```

(2) INFORMATION FOR SEQ ID NO: 47:

(i) SEQUENCE CHARACTERISTICS:
        (A) LENGTH:420
        (B) TYPE:nucleic acid
        (C) STRANDEDNESS:single
        (D) TOPOLOGY:linear (i i) MOLECULE TYPE:mRNA (i i i) HYPOTHETICAL:no (i v) ANTI-SENSE:no (v i) ORIGINAL SOURCE:
        (A) ORGANISM:mouse (i x) FEATURE:
        (A) NAME/KEY:Clone 27KA2

(x i) SEQUENCE DESCRIPTION:SEQ ID NO: 47:

```
GCGGCCGCGG  TGAGAACCGT  TTGGGAATTC  ATC  GAG  ACA  CAG  TCC  CAG                      48
                                   Met  Glu  Thr  Gln  Ser  Gln
                                   -20                      -15

GTC  TTT  GTA  TTC  GTG  TTT  CTC  TGG  TTG  TCT  GGT  GTT  GAC  GGA  GAC  ATT        96
Val  Phe  Val  Phe  Val  Phe  Leu  Trp  Leu  Ser  Gly  Val  Asp  Gly  Asp  Ile
```

```
              -10                          -5                            1
GTG ATG ACC CAG TCT CAC AAA TTC ATG TCC ACA TCA GTA GGA GAC AGG         144
Val Met Thr Gln Ser His Lys Phe Met Ser Thr Ser Val Gly Asp Arg
         5                   10                  15

GTC AGT ATC ACC TGC AAG GCC AGT CAG GAT GTG AAT ACT GCT GTA GCC         192
Val Ser Ile Thr Cys Lys Ala Ser Gln Asp Val Asn Thr Ala Val Ala
         20                  25                  30

TGG TAT CAA CAG AAA CCA GGA CAA TCT CCT AAA CTA CTG CTT TAC TCG         240
Trp Tyr Gln Gln Lys Pro Gly Gln Ser Pro Lys Leu Leu Leu Tyr Ser
 35                  40                  45                  50

GCA TCC TAC CGG TAC ACT GGA GTC CCT GAT CAC TTC ACT GGC AGT GGA         288
Ala Ser Tyr Arg Tyr Thr Gly Val Pro Asp His Phe Thr Gly Ser Gly
             55                  60                  65

TCT GGG ACG GAT TTC ACT TTC ACC ATC AGC GGT GTG CAG GCT GAA GAC         336
Ser Gly Thr Asp Phe Thr Phe Thr Ile Ser Gly Val Gln Ala Glu Asp
                 70                  75                  80

CTG GCA GTT TAT TAC TGT CAG CAA CAT TAT AGT CCT CCT CTC ACG TTC         384
Leu Ala Val Tyr Tyr Cys Gln Gln His Tyr Ser Pro Pro Leu Thr Phe
             85                  90                  95

GGT GCT GGG ACC AAG CTG GAA CTG AAA CGG GCT GAT                         420
Gly Ala Gly Thr Lys Leu Glu Leu Lys Arg Ala Asp
         100                 105                 110
```

( 2 ) INFORMATION FOR SEQ ID NO: 48:

( i ) SEQUENCE CHARACTERISTICS:
        ( A ) LENGTH:360 base pairs
        ( B ) TYPE:nucleic acid
        ( C ) STRANDEDNESS:single
        ( D ) TOPOLOGY:linear ( i i ) MOLECULE TYPE:mRNA ( i i i ) HYPOTHETICAL:no ( i v ) ANTI-SENSE:no ( v i ) ORIGINAL SOURCE:
        ( A ) ORGANISM:mouse ( i x ) FEATURE:
        ( A ) NAME/KEY:Clone 23KA26

( x i ) SEQUENCE DESCRIPTION:SEQ ID NO:48:

```
GGT GTT GAC GGA GAC ATT GTG ATG ACA CAG TCT CAC AAA TTC ATG TCC         48
Gly Val Asp Gly Asp Ile Val Met Thr Gln Ser His Lys Phe Met Ser
             1                   5                  10

ACA TCA GTT GGA GAC AGG GTC ACC ATC ACC TGC AAG GCC AGT CAG GAT         96
Thr Ser Val Gly Asp Arg Val Thr Ile Thr Cys Lys Ala Ser Gln Asp
                 15                  20                  25

GTG ACT ACT GAT GTA GCC TGG TAT CAA CAG AAA CCA CGA CAA TCT CCT         144
Val Thr Thr Asp Val Ala Trp Tyr Gln Gln Lys Pro Arg Gln Ser Pro
             30                  35                  40

AAA CTA CTG ATT TAC TCG GCA TCC TAT CGG TAC ACT GGA GTC CCT GAT         192
Lys Leu Leu Ile Tyr Ser Ala Ser Tyr Arg Tyr Thr Gly Val Pro Asp
 45                  50                  55

CGC TTC ACT GGC AGT GGA TCT GGG ACG GAT TTC ACT TTC ACC ATC AGC         240
Arg Phe Thr Gly Ser Gly Ser Gly Thr Asp Phe Thr Phe Thr Ile Ser
 60                  65                  70                  75

AGT GTG CAG GCT GAA GAC CTG GCA GTT TAT TAC TGT CAG CAA CAT TAT         288
Ser Val Gln Ala Glu Asp Leu Ala Val Tyr Tyr Cys Gln Gln His Tyr
                 80                  85                  90

AGT ACT GCG TGG ACG TTC GGT GGT GGC ACC AAG CTG GAA ATC AAA CCG         336
Ser Thr Ala Trp Thr Phe Gly Gly Gly Thr Lys Leu Glu Ile Lys Arg
         95                  100                 105
```

```
GCT  GAT  GCT  GCA  CCA  ACT  GTA  TCC                                    360
Ala  Asp  Ala  Ala  Pro  Thr  Val  Ser
     110                      115
```